(12) United States Patent
Belkin et al.

(10) Patent No.: US 11,266,710 B2
(45) Date of Patent: Mar. 8, 2022

(54) ANGIO-3 FOR TREATMENT OF RETINAL ANGIOGENIC DISEASES

(71) Applicants: SINGAPORE HEALTH SERVICES PTE LTD, Singapore (SG); NATIONAL UNIVERSITY OF SINGAPORE, Singapore (SG)

(72) Inventors: Michael Belkin, Givat Shumuel (IL); Veluchamy Amutha Barathi, Singapore (SG); Rajamani Lakshminarayanan, Singapore (SG); R. Manjunatha Kini, Singapore (SG); Ge Ruowen, Singapore (SG); Tien Yin Wong, Singapore (SG); Gemmy Chui Ming Cheung, Singapore (SG)

(73) Assignee: Singapore Health Services Pte Ltd., Singapore (SG)

( * ) Notice: Subject to any disclaimer, the term of this patent is extended or adjusted under 35 U.S.C. 154(b) by 0 days.

(21) Appl. No.: 16/641,978

(22) PCT Filed: Aug. 31, 2018

(86) PCT No.: PCT/IB2018/056685
§ 371 (c)(1),
(2) Date: Feb. 25, 2020

(87) PCT Pub. No.: WO2019/043649
PCT Pub. Date: Mar. 7, 2019

(65) Prior Publication Data
US 2020/0246417 A1  Aug. 6, 2020

Related U.S. Application Data

(60) Provisional application No. 62/553,051, filed on Aug. 31, 2017.

(51) Int. Cl.
| | |
|---|---|
| *A61K 38/08* | (2019.01) |
| *A61K 38/16* | (2006.01) |
| *A61K 9/00* | (2006.01) |
| *A61P 27/02* | (2006.01) |
| *C07K 7/06* | (2006.01) |
| *C07K 7/00* | (2006.01) |
| *C07K 14/00* | (2006.01) |

(52) U.S. Cl.
CPC ............ *A61K 38/08* (2013.01); *A61K 9/0048* (2013.01); *A61P 27/02* (2018.01)

(58) Field of Classification Search
CPC .... A61K 38/08; A61K 9/0019; A61K 9/0048; A61K 9/00; A61K 38/16; A61P 27/02; C07K 7/06; C07K 7/00; C07K 14/00
USPC .......... 514/1.1, 13.3, 20.8, 21.6, 21.5, 21.4, 514/21.3, 21.2; 530/300, 324, 325, 326, 530/327, 328
See application file for complete search history.

(56) References Cited

U.S. PATENT DOCUMENTS

| | | | |
|---|---|---|---|
| 2002/0103129 A1 | 8/2002 | Ge et al. | |
| 2003/0064926 A1 | 4/2003 | Folkman et al. | |
| 2006/0122374 A1* | 6/2006 | Mertins ................. | A61P 31/10 530/362 |
| 2006/0193830 A1 | 8/2006 | Hauswirth et al. | |
| 2016/0297854 A1 | 10/2016 | Ghosh et al. | |

FOREIGN PATENT DOCUMENTS

| | | |
|---|---|---|
| CN | 101942012 A | 1/2011 |
| WO | 96/35774 A2 | 11/1996 |
| WO | 97/12625 A1 | 4/1997 |
| WO | 01/18030 A2 | 3/2001 |

OTHER PUBLICATIONS

International Application No. PCT/IB2018/056685, International Search Report and Written Opinion dated Mar. 22, 2019, 27 pages.
Search Report and Written Opinion, Singapore Patent Application No. 11202001595S, dated Sep. 7, 2021, 8 pages.
Extended European Search Report,EP Pat. Appl. No. 18851201.6, dated Apr. 14, 2021, 7 pages.

\* cited by examiner

*Primary Examiner* — Julie Ha
(74) *Attorney, Agent, or Firm* — Kilpatrick Townsend & Stockton LLP

(57) ABSTRACT

This disclosure provides methods of a method of treating a retinal angiogenic in a subject comprising administering an effective amount of an Angio-3 peptide.

11 Claims, 38 Drawing Sheets
Specification includes a Sequence Listing.

Transgenic hVEGF mice- Control

Transgenic hVEGF mice-Treated

Treatment commenced at 6-7 weeks old mice:

- Eylea (positive control) is effective for 4 weeks post treatment.
- Angio-3 (test peptide) is effective for 16 weeks post treatment.

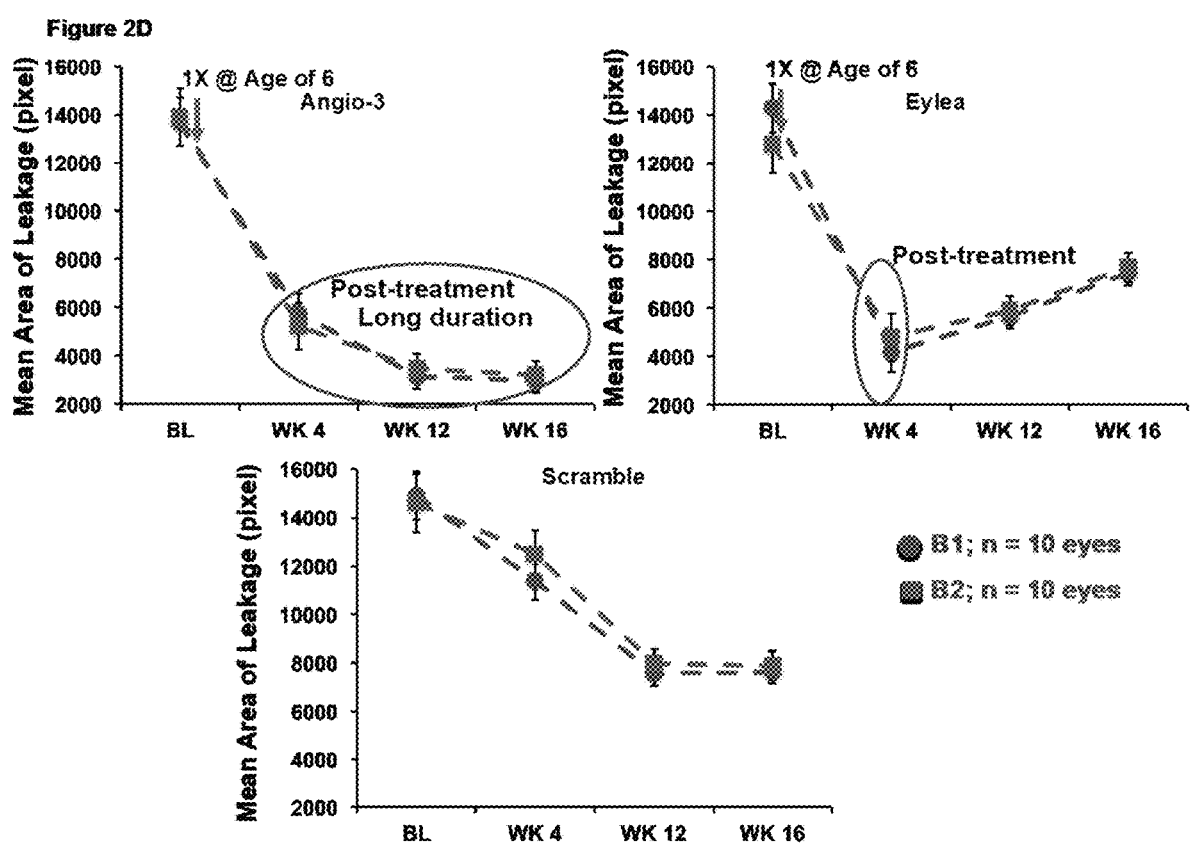

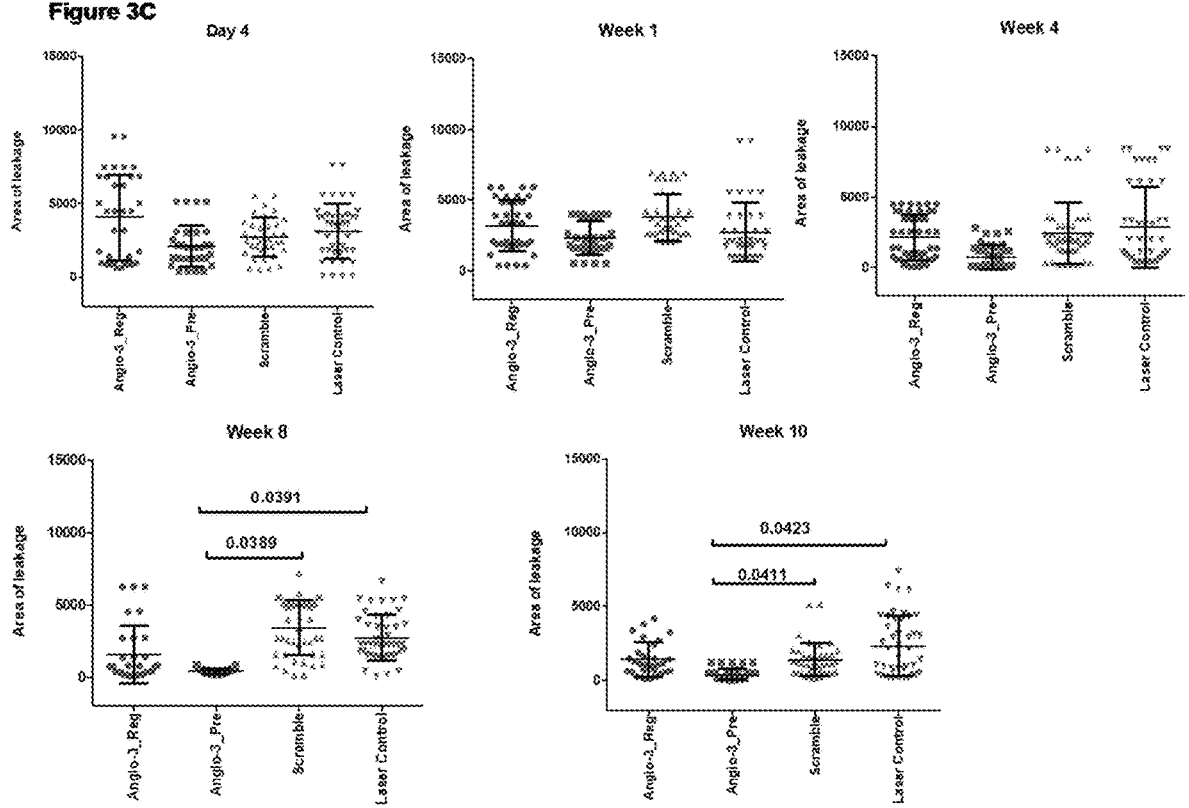
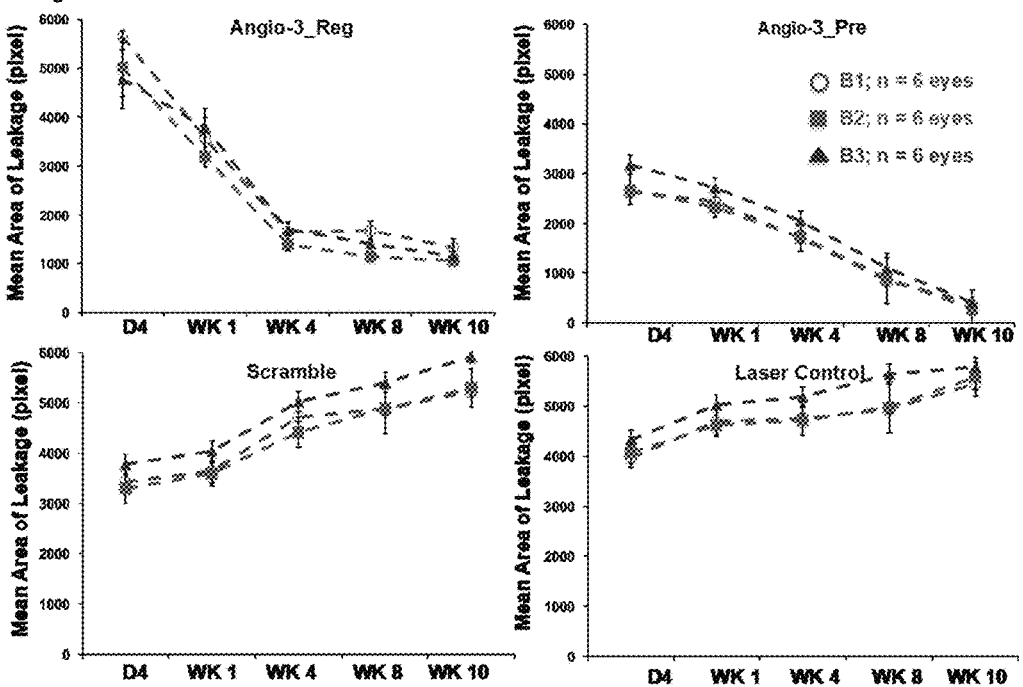

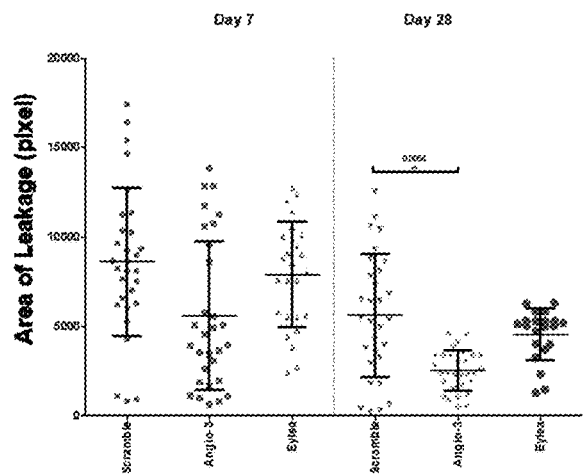
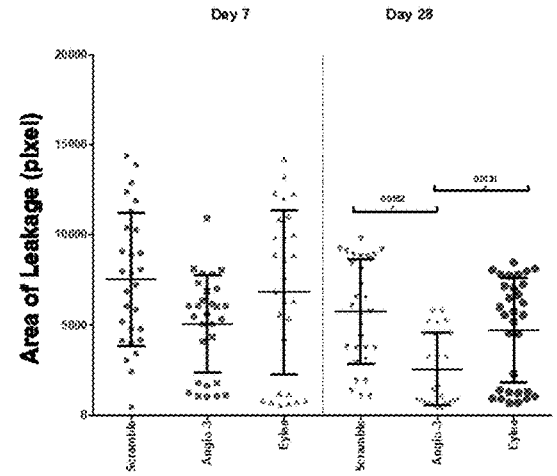
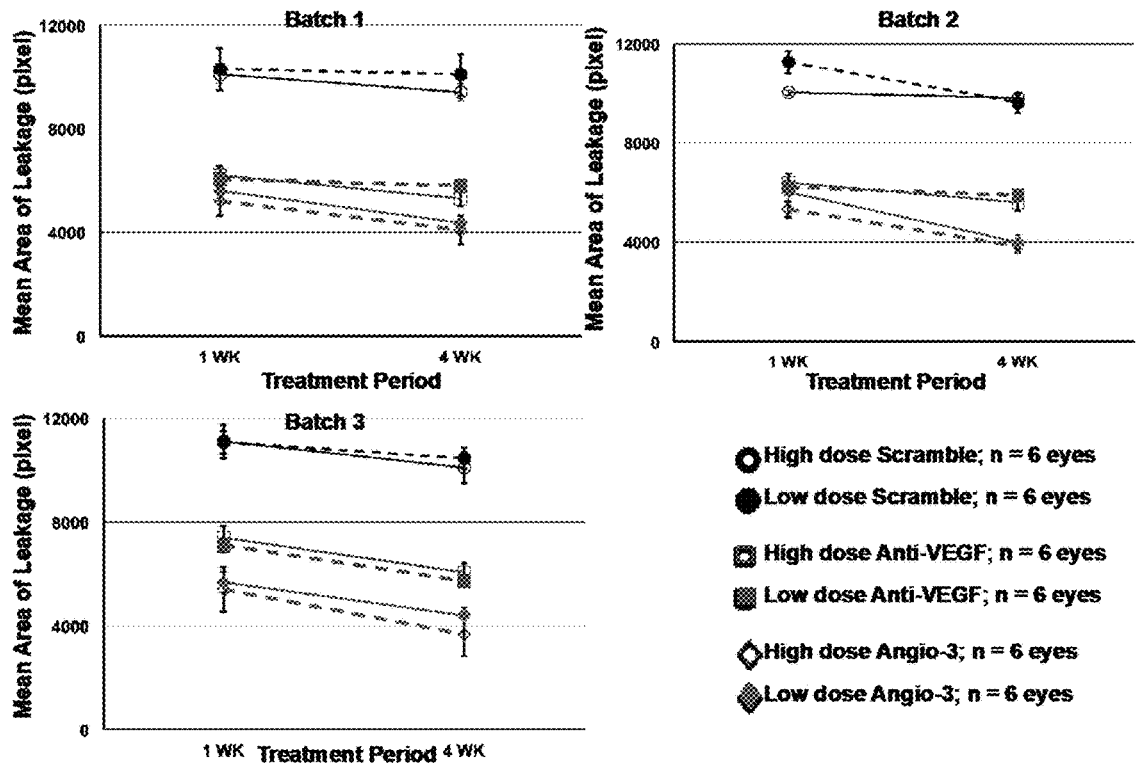
Figure 4B, Figure 4C

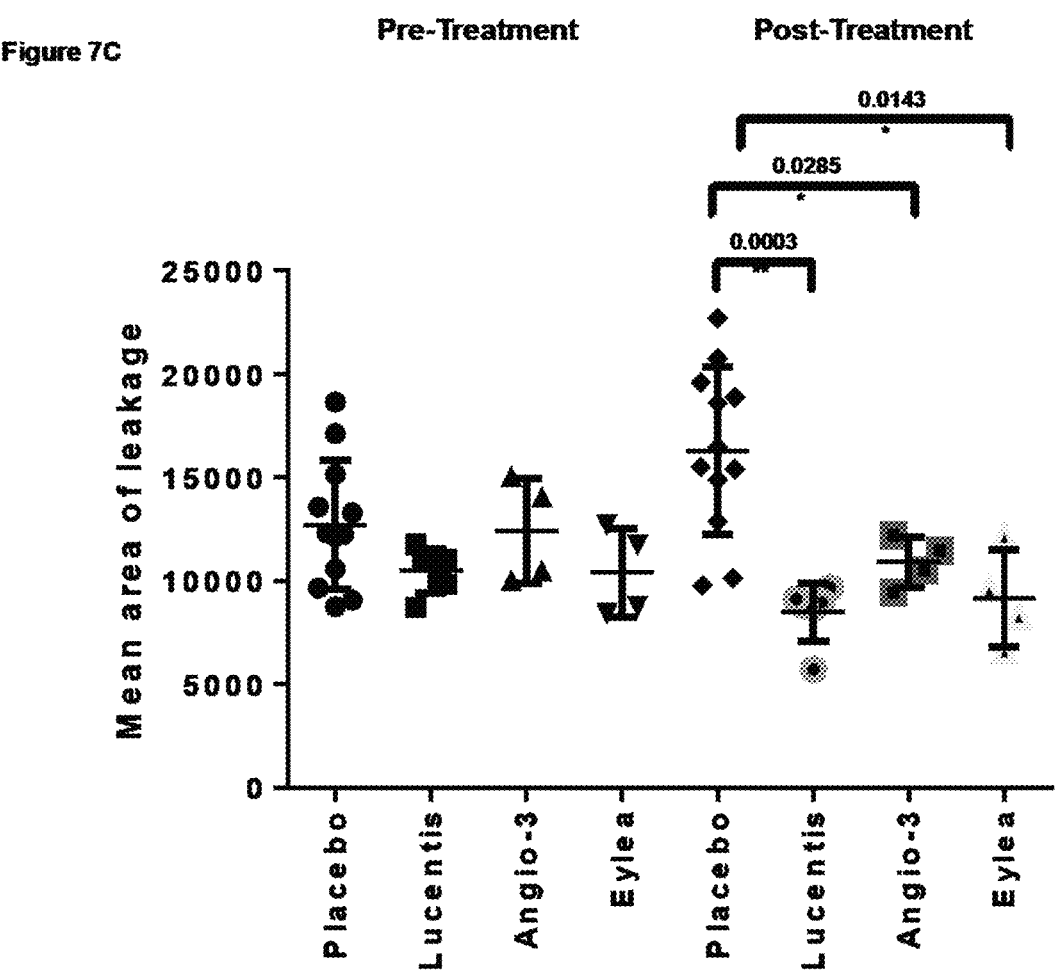

A.

B

A

B

A

B

FFA Quantification (laser area)

PS-OCT Quantification (laser volume)

ANGIO-3 FOR TREATMENT OF RETINAL ANGIOGENIC DISEASES

CROSS-SECTION TO RELATED APPLICATIONS

This application is a U.S. National Phase of International Application No. PCT/IB2018/056685, filed Aug. 31, 2018, which claims priority to U.S. Patent Application No. 62/553,051, filed Aug. 31, 2017, the disclosure of which is hereby incorporated by reference in its entirety for purposes.

BACKGROUND

The Sequence Listing written in file 101286_1177050_Sequence_Listing.txt created on Feb. 21, 2020, containing 1,331 bytes, machine format IBM-PC, MS-Windows operating system, is hereby incorporated by reference in its entirety. Retinal angiogenic diseases include age-related macular degeneration, retinopathy, vascular occlusion, diabetic retinopathy, diabetic macular edema, central retinal vein occlusion, branch retinal vein occlusion, and corneal neovascularization. Retinal angiogenic disease, e.g., age-related macular degeneration (AMD), is the most frequent cause of legal blindness in the elderly in industrialized countries (Van Leeuwen et al. (2003), European Journal of Epidemiology 18: 845-854). It is a heterogeneous disease, which is characterized by progressive loss of central, high acuity vision. For the patient it dramatically compromises quality of life, as they lose their ability to read, to recognize faces, and day-to-day tasks become major obstacles. According to the World Health Organization (WHO) a total of 30-50 million individuals are affected and about 14 million people are blind or severe visual impairment due to AMD (Gehrs et al., (2006) Annals of Medicine 38:450-471).

The pathological process responsible for retinal angiogenic diseases is the formation of chaotically oriented and physiologically deficient new blood vessels under the retina, known as choroidal neovascularization (CNV). Although aging, oxidative stress, genetics and inflammation have all been described to contribute to the pathogenesis of CNV; angiogenesis is currently believed to be responsible for the final common pathway.

Current treatment options for AMD include laser therapy, surgery to remove or destroy the abnormal blood vessels, and anti-angiogenic therapies, e.g., anti-vascular endothelial growth factor ("VEGF"), i.e., anti-VEGF therapies. These anti-angiogenic medications are typically injected into the vitreous body of the eye, which cause great discomfort and inconvenience to the patients. In addition, some patients have developed resistance to anti-VEGF therapy and are in need of other treatment options. Yang et al., Drug. Des. Devel. Ther. 2016: 10:1857-1867.

BRIEF SUMMARY

Provided herein is a method of treating a retinal angiogenic disease in a subject. The methods include administering to the subject a pharmaceutically effective amount of a composition comprising a peptide having the sequence Thr Pro His Thr His Asn Arg Thr Pro Glu (SEQ ID NO:1). The composition can be administered to the subject orally, by intravenous injection, or by intravitreal injection, or by sublingual delivery wherein administration treats the retinal angiogenic disease in the subject.

Optionally, the composition comprises 2 to 50 mg/kg body weight (Bwt) of the peptide and is administered by intravenous injection. Optionally, the composition comprises 0.1 µg/kg to 5 mg/kg Bwt of the peptide and is administered by intravitreal injection. Optionally, the composition comprises 2 to 10 mg/kg Bwt of the peptide and is administered orally.

Optionally, the composition is administered via either intravenous (IV) or intravitreal (IVT) route at least once every 4 to 24 weeks. Optionally, the composition is administered orally at least once daily for 1 to 2 weeks at intervals of 6 months. In this treatment protocol, the composition is not administered during the 6 month interval. Optionally, for the subject not responsive to anti-VEGF therapy, for example, a VEGF antibody.

Optionally, the subject has age-related macular degeneration, retinopathy, or vascular occlusion. Optionally, the subject has diabetic retinopathy, diabetic macular edema, central retinal vein occlusion, branch retinal vein occlusion, or corneal neovascularization. Optionally, the subject is a human.

Also provided herein is a method of treating a retinal angiogenic disease in a subject. The methods include selecting a subject with retinal angiogenic disease not responsive to an anti-angiogenesis therapy, and administering to the subject a composition comprising a peptide having the sequence SEQ ID NO:1, wherein administration treats the retinal angiogenic disease in the subject. Optionally, the subject is not responsive to an anti-VEGF therapy.

Optionally, the composition disclosed herein is formulated for intravenous administration, for intravitreal injection, or for oral administration. Optionally, the subject has age-related macular degeneration, retinopathy, or vascular occlusion. Optionally, the subject has diabetic retinopathy, diabetic macular edema, central retinal vein occlusion, branch retinal vein occlusion, or corneal neovascularization. Optionally, the subject is not responsive to anti-angiogenesis therapy. Optionally, the subject is not responsive to anti-VEGF therapy, e.g., a VEGF antibody. Optionally, the subject is a human.

Also provided is a method of treating a retinal angiogenic disease in a subject. The method includes administering to the subject a pharmaceutically effective amount of a composition comprising a peptide N having the sequence Thr Pro His Thr His Asn Xaa Thr Pro Glu wherein Xaa is homoarginine (SEQ ID NO:3). The composition can be administered to the subject orally, by intravenous injection, or by intravitreal injection, wherein administration treats the retinal angiogenic disease in the subject.

Also provided is a method of treating a retinal angiogenic disease in a subject. The method includes administering to the subject a pharmaceutically effective amount of a composition comprising a peptide Q having the sequence Thr Pro His Thr His Gln Xaa Thr Pro Glu wherein Xaa is homoarginine (SEQ ID NO:4), wherein the composition is administered to the subject orally, by intravenous injection, or by intravitreal injection, wherein administration treats the retinal angiogenic disease in the subject.

BRIEF DESCRIPTION OF THE DRAWINGS

FIG. 1A is a schematic of the experimental design. FIG. 1B are images showing Fundus Fluorescein Angiography (FFA) images of baseline and weekly after post treatment. Digital color fundus photographs were taken using a MICRON IV comprehensive system for rodent retinal imaging (Phoenix Research Labs, Pleasanton, Calif.) after pupil dilatation with topical administration of 1% tropicamide (Alcon Laboratories, Inc., Fort Worth, Tex.) and 2.5% phenylephrine (Bausch and Lomb Pharmaceuticals, Inc., Tampa, Fla.) ophthalmic solutions. For FFA, mice were injected intraperitoneally with 10% sodium fluorescein dye at a dose of 0.01 mL/5-6 g BWt and fundus images were obtained using MICRON IV. FIG. 1C is a graph showing regression of leakage in Kimba mice by each eye and by batch. IV single injection of 100 μL of Angio-3 was given at week 4 and followed for further 4 weeks. (25 mg/Kg Bwt). Readout is the leakage of retinal vascularization post-administration of the drug. n=6 eyes per batch; n=3 batches; Values are expressed as means±s.e.m., **P<0.01, *P<0.05, student's t-test. FIG. 1D are images showing Isolectin Retinal staining. Control and Angio-3 treated eyes were enucleated and fixed in 4% paraformaldehyde (PFA) in PBS for 15 minutes at room temperature. The eyes were then transferred to cold 1×PBS on ice for 5-10 minutes. The neural retina and choroid/RPE were dissected separately and placed in cold (−70° C.) ethanol. Retinas were then rinsed in PBS and blocked in 1% Triton-X/PBS for 30 min. The whole mounts were then incubated with Isolectin GS-IB4 from Griffonia Simplicofolia, Alexa Fluor 594 Conjugate (Molecular Probes, 121413 1:100) overnight at 4° C. Stained whole mounts were flat-mounted with Prolong Gold (Invitrogen) and left overnight. All imaging was performed with a laser-scanning confocal fluorescence microscope.

FIGS. 2A, 2B, 2C and 2D show the efficacy of a single IVT dose of angio-3 and Eylea (anti-VEGF), positive control in attenuating the retinal angiogenesis in KIMBA mice. FIG. 2A is a schematic of the experimental design. FIG. 2B are images showing Fundus Fluorescein Angiography (FFA) images of baseline and weekly after post treatment. FIG. 2C is a graph showing regression of leakage in Kimba mice by each eye. FIG. 2D are graphs showing regression of leakage in Kimba mice by batch. IVT single injection of 1 μg in 1 μL of Angio-3 scramble; Angio-3 peptide and Eylea was given at week 7 and followed for further 16 weeks. Readout is the leakage of retinal vascularization post-administration of the drug. n=10 eyes per batch; n=2 batches; Values are expressed as means±s.e.m., **P<0.01, *P<0.05, student's t-test. The results showed that treating with Eylea (positive control) is effective in attenuating retinal angiogenesis for 4 weeks post treatment and treating the mice with angio-3 is effective in attenuating retinal angiogenesis for 16 weeks post treatment.

FIG. 3C is a graph showing the area of leakage by each eye for various groups. FIG. 3D are graphs of the mean area of leakage of all batches for each group. Single dose of Angio-3 decreased the lesions in a laser-induced mice CNV model in both prevention and regression mode via IV route till 10 weeks and this was very significant in prevention mode. The attenuation retinal vascularization was better than scrambled peptide. n=6 eyes per batch; n=3 batches. Values are expressed as means±s.e.m., **P<0.01, *P<0.05, student's t-test.

FIG. 4B are graphs of the area of leakage by each eye for various groups and FIG. 4C shows the mean area of leakage of all batches for each group. This figure illustrates that a single dose Angio-3 significantly reduced angiogenesis as compared to Eylea (anti-VEGF) and scrambled peptide in a laser-induced mice CNV model via IVT route. n=6 eyes per batch; n=3 batches; Values are expressed as means±s.e.m., **P<0.01, *P<0.05, student's t-test.

FIG. 7B are images of fundus fluorescein angiography ("FFA") of the eye in monkeys treated with a single dose (2 mg) of Angio-3, anti-VEGF (Eylea and Lucentis) in laser induced monkey CNV model via IVT route. FIG. 7C is a graph showing regression of leakage was plotted by each eye in each group before and after treatment. n=2 monkeys per group; Values are expressed as means±s.e.m., ***P<0.001, *P<0.05, student's t-test.

Control sections showed more choroidal fibroplasia, increased retinal thickness, more choroidal neovascularization, multiple vessels extending once or twice the retinal thickness and retinal elevation as compared to drug-treated eyes.

FIG. 11 A are FFA images of baseline and at different time points post treatment. Mice received single IVT injection of Angio-3 (at a dose of 1 μg in 1 μl or 100 ng in 1 μl), and chemically modified Angio-3 peptides Pep-N (at doses of 5 μg in μl; 1 μg in μl; and 100 ng in 1 μl, respectively) and Pep-Q peptides (at doses of 5 μg in μl; 1 μg in μl; and 100 ng in 1 μl, respectively). FIG. 11 B is a graph of the area of leakage by each eye. Single dose attenuates retinal angiogenesis in laser-induced mice CNV model via IVT route till 4 weeks. All three peptides were able to significantly attenuate the choroidal angiogenesis in laser-induced CNV mouse model. Eylea is the positive control. n=18 eyes per group; Values are expressed as means±s.e.m. n=3 independent experiment, **P<0.01, *P<0.05, student's t-test.

Figure 12:
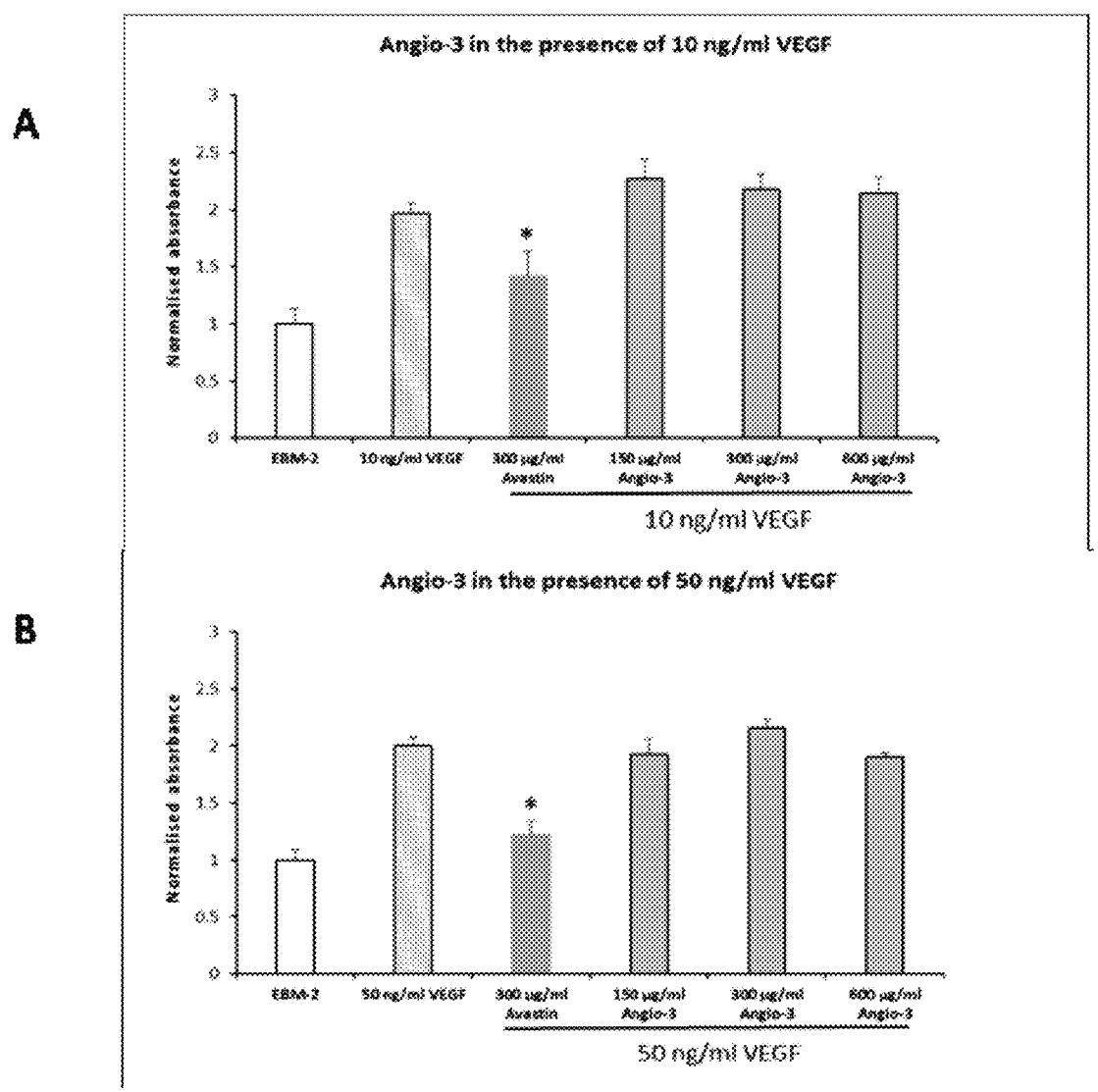

FIGS. 12A and 12B illustrates effect of Angio-3 on VEGF induced cell proliferation of HRMECs. FIG. 12A is a graph showing the effect of Angio-3 in combination of 10 ng/ml VEGF. FIG. 12B is a graph showing the effect of Angio-3 in combination of 50 ng/ml VEGF.

Figure 13:
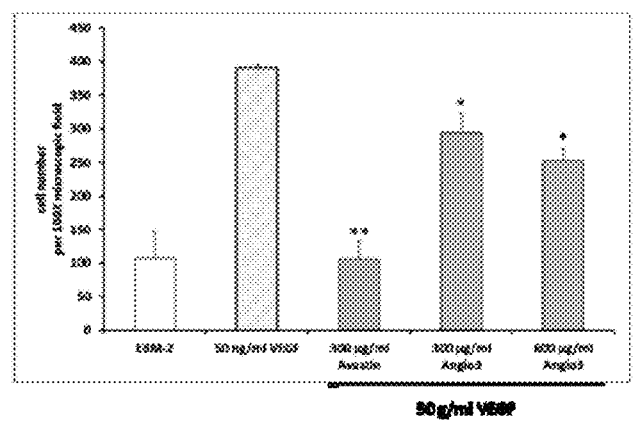
Figure 13:
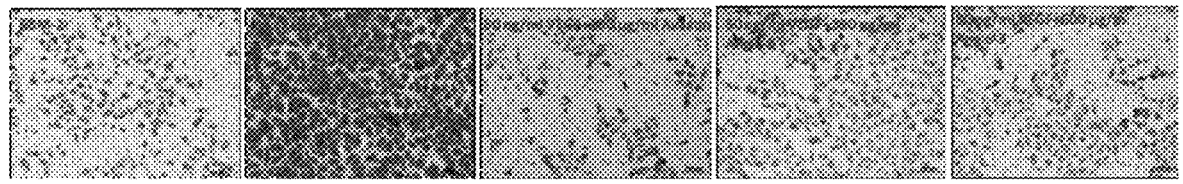

FIGS. 13A and 13B show effect of Angio-3 on HRMEC cells migration in the presence of: 1) in EBM-2 alone, 2) EBM-2 supplemented with 50 ng/ml VEGF, 3) EBM-2 supplemented with 300 ug/ml Avastin plus 50 g/ml VEGF, 4) EBM-2 supplemented with 300 ug/ml Angio3 plus 50 g/ml VEGF, and 5) EBM-2 supplemented with 600 ug/ml Angio3 plus 50 g/ml VEGF. FIG. 13B are FFA images and FIG. 13A is a graph of the number of cells in microscopic fields under 100× objective based on the images of FIG. 13B.

FIGS. 14A and 14B show effect of Angio-3 on VEGF induced HRMECs tube formation in the presence of: 1) in EBM-2 alone, 2) EBM-2 supplemented with 50 ng/ml VEGF, 3) EBM-2 supplemented with 300 ug/ml Avastin plus 50 g/ml VEGF, 4) EBM-2 supplemented with 300 ug/ml Angio3 plus 50 g/ml VEGF, and 5) EBM-2 supplemented with 600 ug/ml Angio3 plus 50 g/ml VEGF. FIG. 14B are FFA images of cells. FIG. 14A is a graph of quantifications of total tube length, number of junctions, and total number of loops based on the images in FIG. 14B. **P<0.01, *P<0.05. Unless explicitly noted otherwise, the VEGF peptide disclosed in this application refers to $VEGF_{165}$, a subtype of human VEGF that has the most potent biological activity and is the most abundantly present in vivo.

Figure 15:
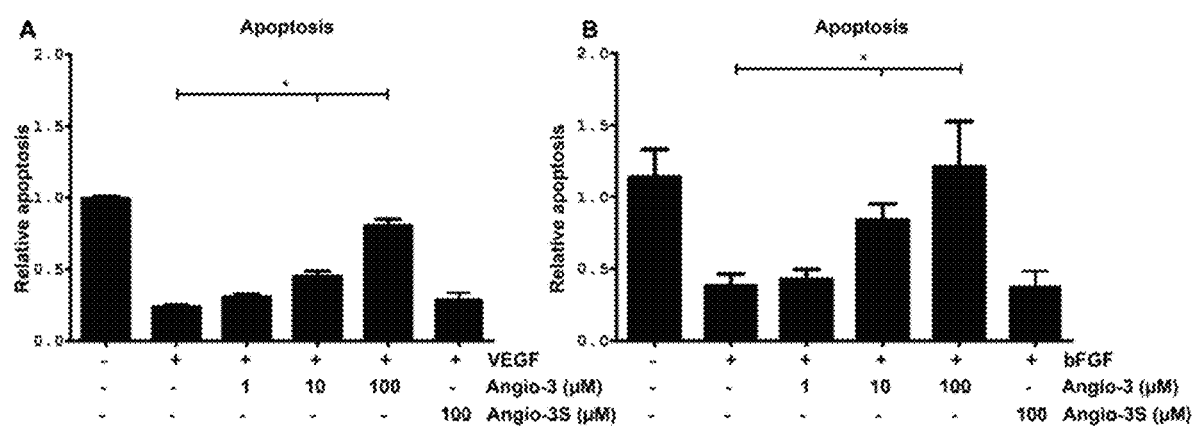

FIGS. 15A and 15B are graphs showing that Angio-3 induced human umbilical vein endothelial cells (HUVECs) apoptosis in the presence of either VEGF or bFGF. FIG. 15A shows Angio-3 induced HUVEC apoptosis in the presence of 20 ng/ml VEGF in a dose-dependent manner. FIG. 15B shows that Angio-3 induced HUVEC apoptosis in the presence of 20 ng/ml bFGF in a dose-dependent manner. * represents p<0.05, n=3.

Figure 16:
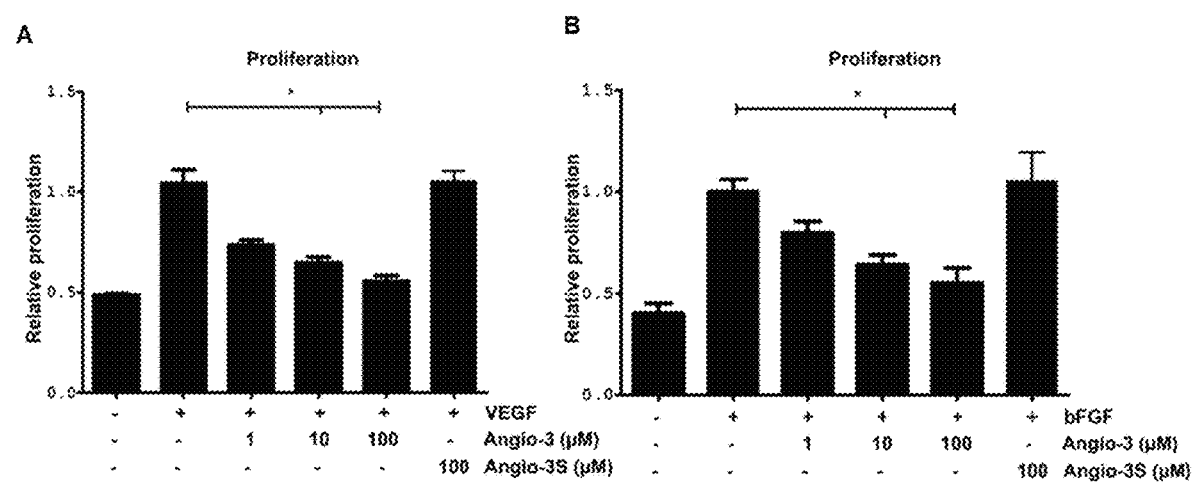

FIGS. 16A and 16B are graphs showing Angio-3 inhibited HUVEC proliferation stimulated by VEGF and bFGF. FIG. 16A shows Angio-3 suppressed HUVEC proliferation induced by 20 ng/ml VEGF in a dose-dependent manner. FIG. 16B shows Angio-3 suppresses HUVEC proliferation induced by 20 ng/ml bFGF in a dose-dependent manner. * represents p<0.05, n=3.

FIGS. 17A, 17B, 17C and 17D show that Angio-3 inhibited VEGF and bFGF-induced EC migration and inhibits capillary network formation. FIGS. 17 A are images and 17 C is a graph showing Angio-3 suppressed HUVEC chemotactic migration induced by 20 ng/ml VEGF in a dose-dependent manner. Migrated cells were stained with Hoechst, imaged and counted. FIGS. 17 B are images and 17 D is a graph showing Angio-3 suppressed HUVEC chemotactic migration that was induced by 20 ng/ml bFGF in a dose-dependent manner. Migrated cells were stained with Hoechst, imaged and counted. n=3; * represents significant reduction compared to control at P<0.05 by one-way ANOVA.

FIGS. 18A and 18B show that Angio-3 inhibited HUVEC capillary network formation on Matrigel. FIG. 18A are representative images of HUVEC tube formation on Matrigel. HUVECs were pre-incubated with increasing doses of Angio-3 for 30 min prior to seeding on Matrigel. FIG. 18B is a graph of percentage area covered by HUVEC tubes. n=3; * represents significant reduction compared to control at P<0.05 by one-way ANOVA.

Figure 19:
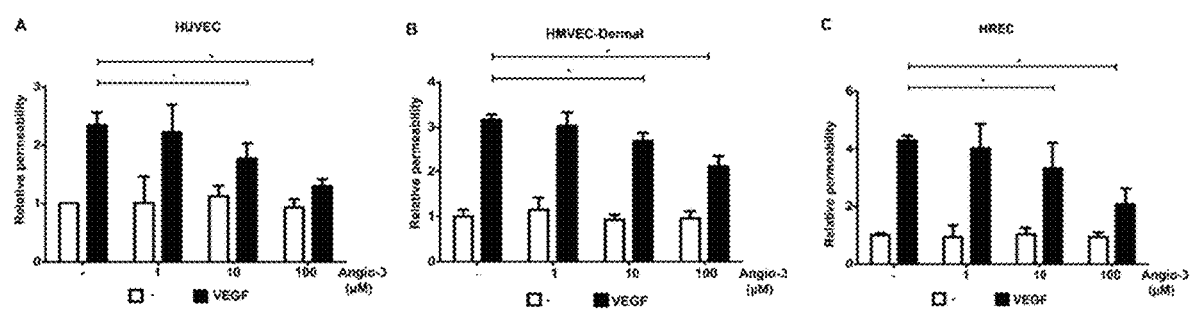

FIGS. 19A, 19B and 19C are graphs showing that Angio-3 is a novel anti-permeability agent that can inhibit VEGF-induced vascular permeability (VP) with multiple endothelial cell types. In FIG. 19A, post-confluent HUVEC monolayers were treated with increasing concentrations of Angio-3 or medium alone. The results show that Angio-3 inhibited VEGF-induced permeability across confluent HUVECs in a dose-dependent manner without affecting the basal level permeability. In these experiments, post-confluent HUVEC monolayers were pre-treated with Angio-3 for 30 minutes prior to stimulation with 100 ng/ml VEGF. In FIG. 19B, Post-confluent HMVEC monolayers were treated with increasing concentrations of Angio-3 or medium alone. The results show that Angio-3 inhibited VEGF-induced permeability across confluent human dermal microvascular endothelial cells (HMVECs) in a dose-dependent manner without affecting the basal level permeability. In FIG. 19C, post-confluent HREC monolayers were treated with Angio-3 and VEGF for 3 h. The results show that Angio-3 inhibited VEGF-induced permeability across confluent human retinal endothelial cells (HRECs) in a dose-dependent manner without affecting the basal level permeability. * represents p<0.05, n=3.

Figure 20:
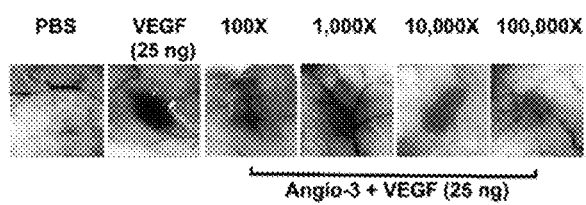
Figure 20:
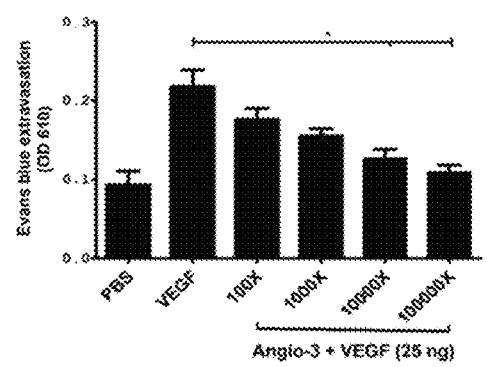

FIGS. 20A and 20B are images and a graph, respectively, showing that Angio-3 inhibited local VEGF-induced dermal vascular permeability in mice. In FIG. 20A, Angio-3 was administered via intradermal injection to mice and the results show that Angio-3 inhibited VEGF-induced dermal permeability in a dose-dependent manner within 15 min. The dermal permeability was visualized by Evans blue dye extravasation. In FIG. 20B, dye extravasation was quantified by formamide extraction of the dye and measuring OD 610. n=5 animals per group, * represent significantly increased as compared with the simultaneous control at p<0.05.

FIGS. 21A, 21B, 21C and 21D are images showing Angio-3 prevented VEGF-induced dissociation of Vascular endothelial ("VE")-cadherin from Adherens junctions (AJs) on HUVECs. Angio-3 protected VE-cadherin from VEGF-induced dissociation from cell-cell AJ. Confluent HUVEC monolayers were pre-treated with 100 μM Angio-3 for 30 min following which the monolayers were stimulated with 100 ng/ml VEGF for 20 min. Cells were then fixed, permeabilized and probed for VE-cadherin. FIGS. 21A-D shows control cells, cells treated with 100 ng/ml VEGF, cells treated with 100 uM Angio-3, and cells treated with 100 ng/ml VEGF plus 100 uM Angio-3, respectively.

FIGS. 22A and 22B are images showing Angio-3 suppressed VEGF-induced dissociation of tight junction (TJ) proteins ZO-1 and ZO-2 from TJs in HUVECs. Cells were treated under control, 100 ng/ml VEGF, 100 μM Angio-3, and 100 ng/ml VEGF plus 100 μM Angio-3, respectively.

FIGS. 23A, 23B, 23C and 23D are images showing Angio-3 suppressed VEGF-induced actin stress fiber formation in HUVECs. However, in the absence of VEGF, Angio-3 promoted cortical actin fiber formation. The red color represents action staining and the blue represent DAPI staining.

Figure 24:
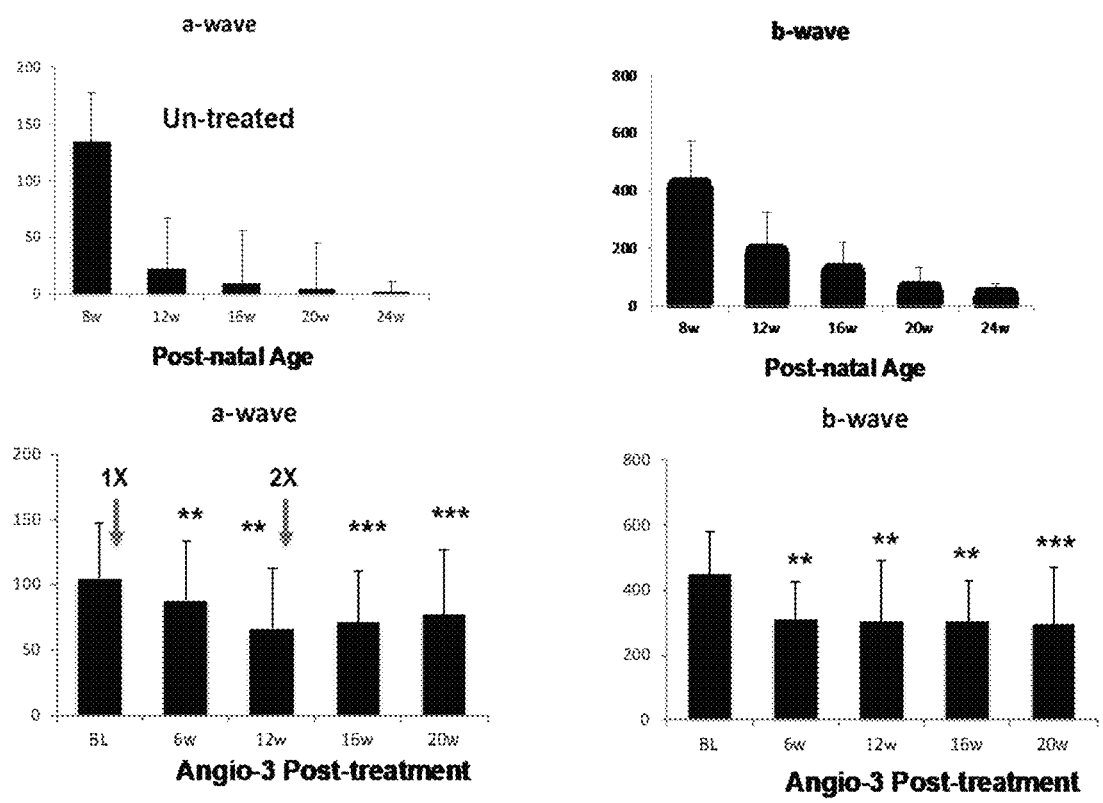

FIG. 24 are graphs showing the results of retinal function tests recorded via electroretinogram (ERG). Untreated mice has no response of both a and b-waves after 12 weeks of age. Angio-3 increased the a and b-wave responses for 6 weeks post treatment and then again increased the response for 20 weeks with second dose. This result shows that Angio-3 is rescuing the retinal function in KIMBA mice. Data is represented as mean±S.D. =P<0.05; *=P<0.01.

Figure 25A:
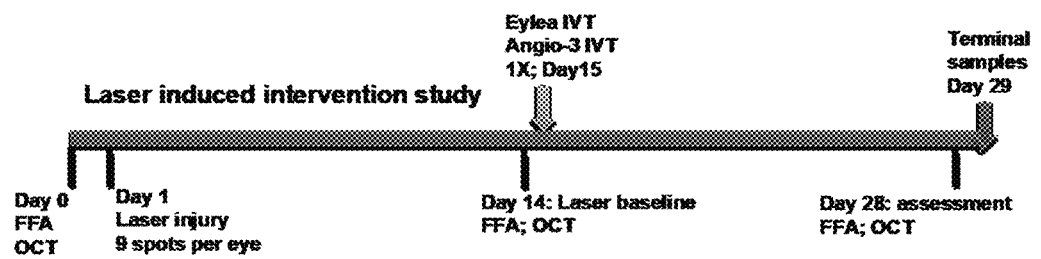
Figure 25B:
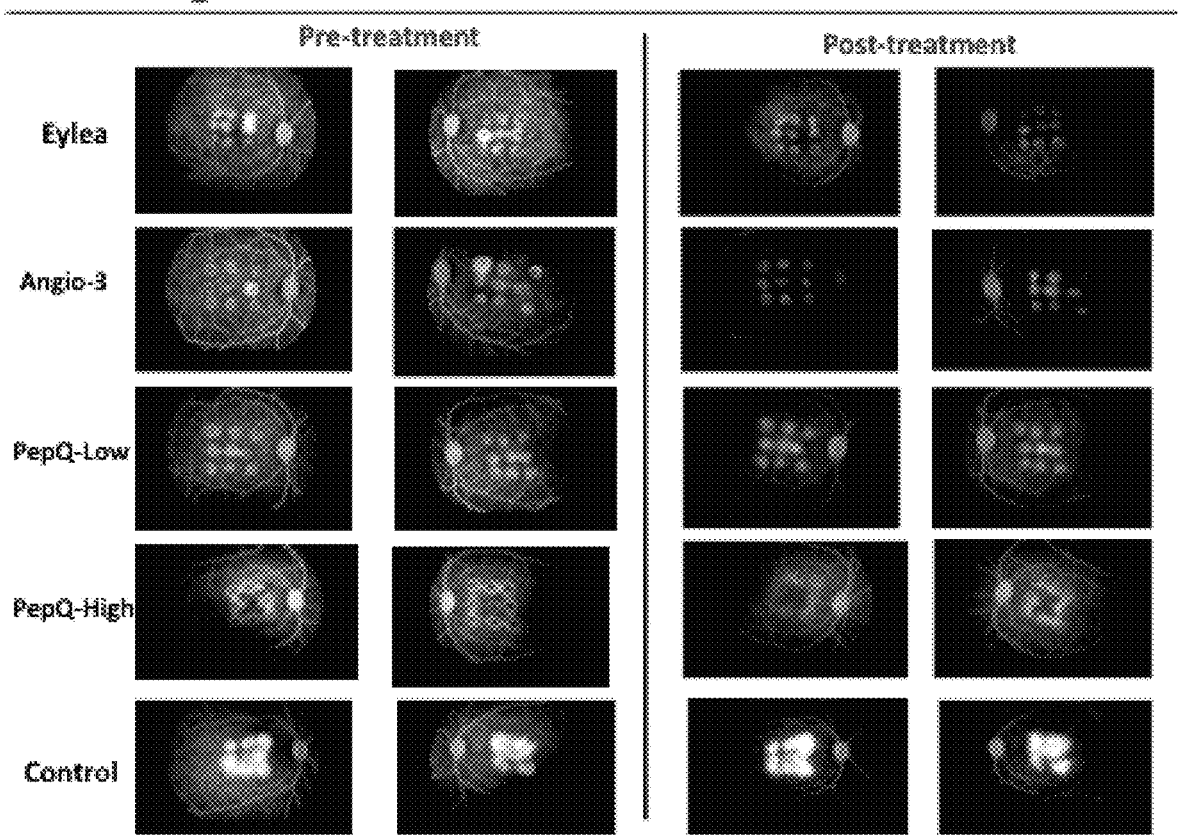
Figure 25C:
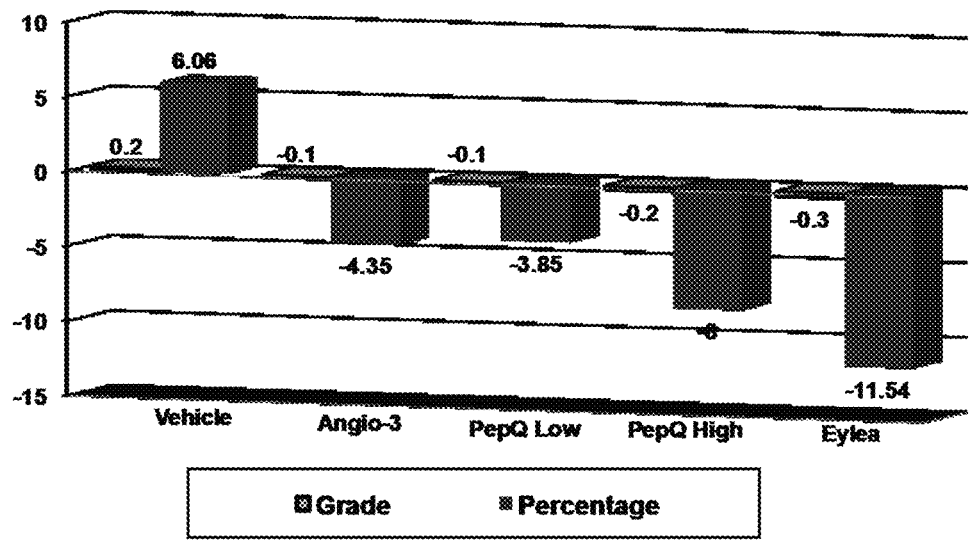
Figure 25D:
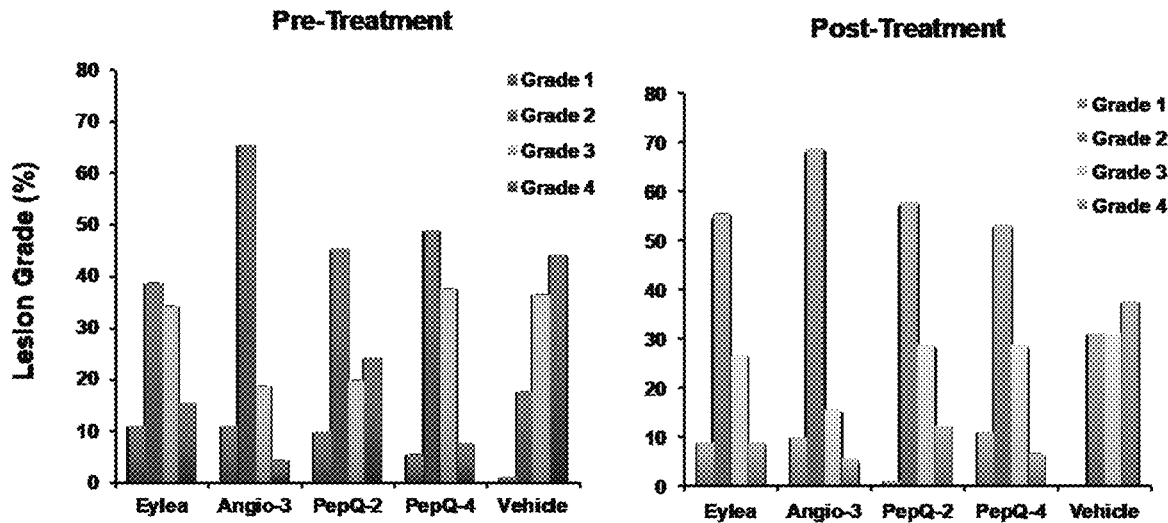
Figure 25E:
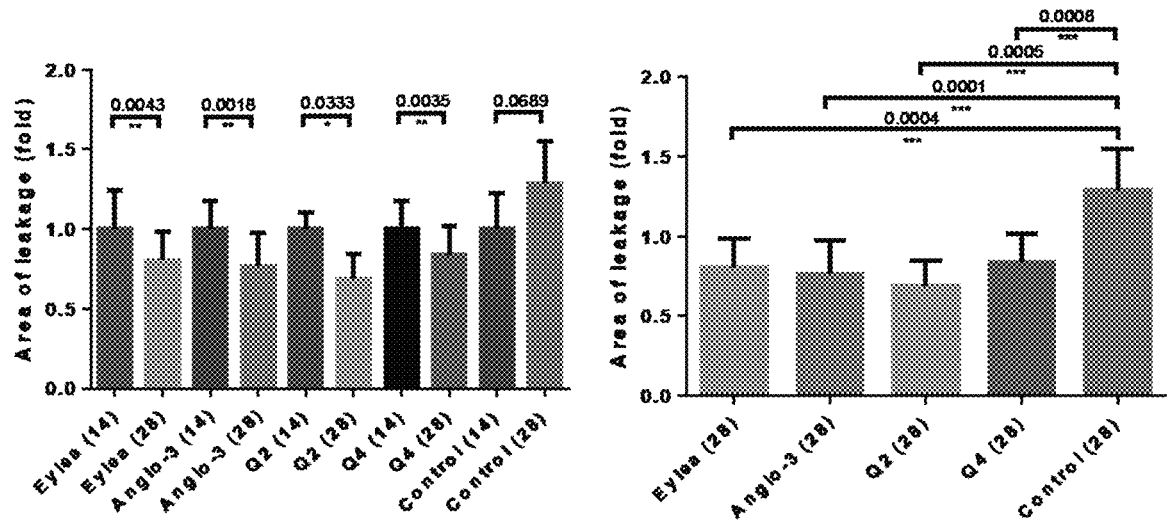
Figure 25F:
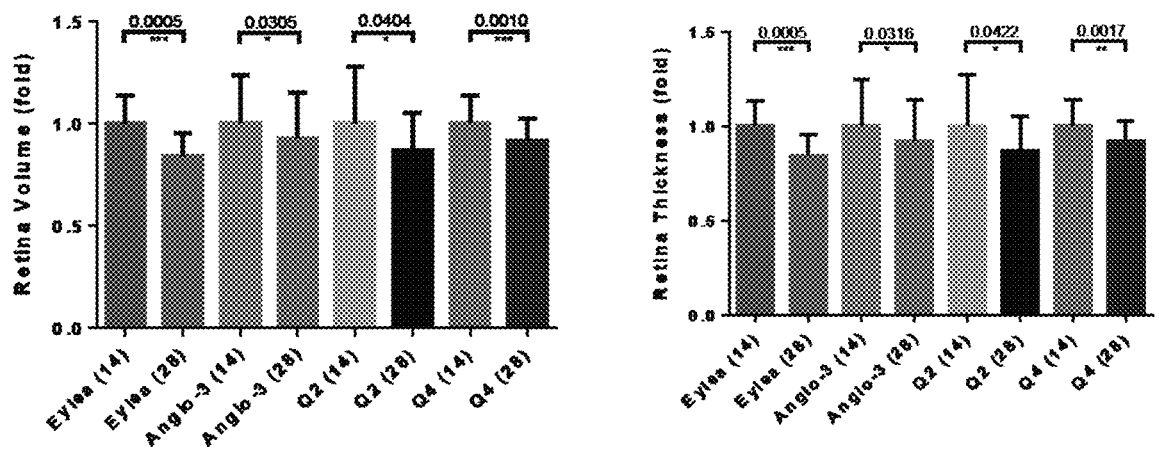

FIGS. 25A, 25B, 25C, 25D, 25E, and 25F show the results of testing in a laser-induced chorodial neovascularization (CNV) model in Cynomolgus moneys developed as an experimental model of wet AMD. FIG. 25A is a schematic of the study design. FIG. 25B are representative fundus fluorescein angiography (FFA) images of all groups. FIG. 25C is a graph showing change in mean lesion grade of the eye in monkeys treated with a single dose 2 mg of Angio-3, dose 2 mg of anti-VEGF (Eylea), 2 mg of peptide (Q2) and 4 mg of peptide (Q4) and control. FIG. 25D is a graph of percentage of all grades pre and post treatment of Angio-3, PepQ-low dose (2 mg); PepQ-high dose (4 mg), Eylea and control eyes that was tested in laser induced choroidal neo-vascularization non-human primate model. FIG. 25E is a graph of laser area quantified from the FFA images by ImageJ software. FIG. 25F are graphs of laser volume quantified from PS-OCT images by ImageJ software. All 4 treated groups significantly reduces leakage and neovessel area as compared to vehicle control. Eylea shows the superior efficacy as compared to test peptides. However, Pep-Q shows dose dependent efficacy and higher dose efficacy is as close to Eylea.

FIGS. 26A and 26B are images showing progression of corneal neovascularization seven days after alkali-burn injury. FIG. 26A are representative image of a vehicle treated eye. FIG. 26B are representative image of an eye treated three times per day with our compound of interest (PeptideQ). White arrow indicates the difference in corneal opacity and neovascularization.

Figure 27:
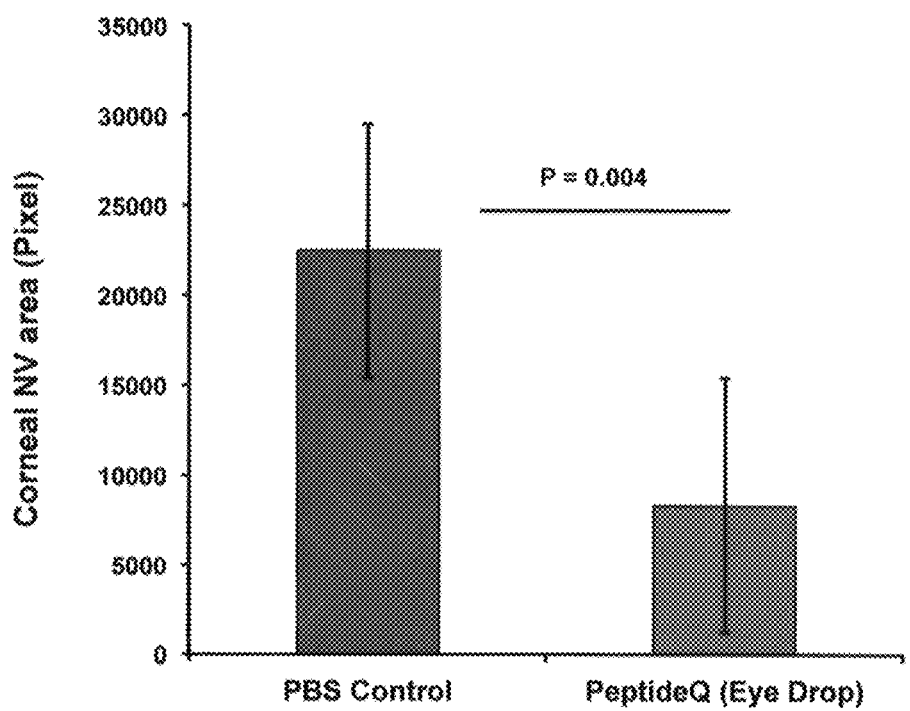

FIG. 27 is a graph of the area of corneal neovascularization (NV) seven days after alkali-burn injury was quantified by ImageJ software. Peptide Q treated eyes were significantly reduced corneal NV area as compared to vehicle control eyes.

Figures 28A, 28B:
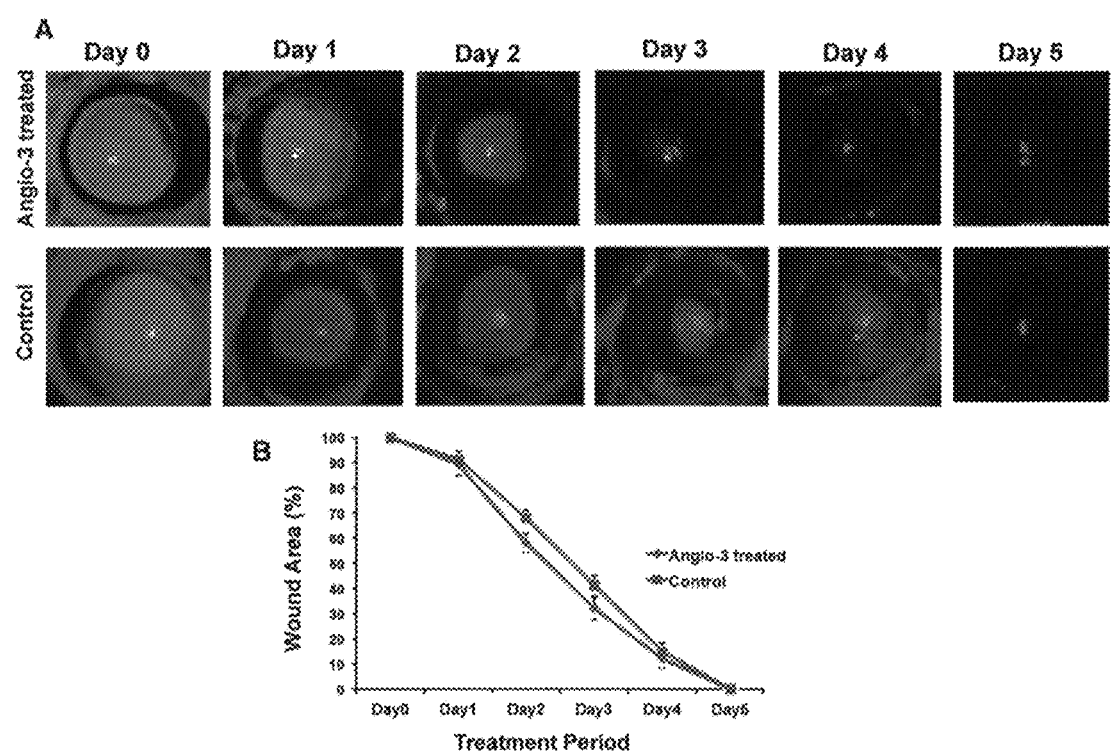

FIGS. 28A and 28B are images and a graph showing results of testing wound healing in a mouse model. FIG. 28A are representative slitlamp biomicroscopy images of murine cornea following the removal of corneal epithelium from Angio-3 treated and control wild-type mice and topical fluorescein staining of the epithelial defect (green). FIG. 28B is a graph of the percentage of wound defect remaining (vertical axis) over time (horizontal axis) in Angio-3 treated and control wild-type mice, n=6 for each group from 2 independent experiments. Both groups are statistically significant. Angio-3 didn't affect the normal wound healing process. Data is represented as mean±S.D.

DETAILED DESCRIPTION

Provided herein are compositions and methods for treating subjects having a retinal angiogenic disease by administering a composition comprising Angio-3 peptides. The Angio-3 peptide acts to block the formation of new vessels in patients having retinal angiogenic disease and is particularly useful for patients who are not responsive to anti-VEGF therapies. The therapy can be conveniently delivered orally or by intravenous injection, or by intravitreal injection.

The term "about" when used in conjunction with a value means any value that is reasonably close to the value, i.e., within the range of +10% of the value. In particular, it would include the value itself. For example, both a value of 45 mg/kg and a value of 55 mg/kg are deemed to be "about 50 mg/kg".

The terms "subject", "patient" or "individual" are used herein interchangeably to refer to a human or animal. For example, the animal subject may be a mammal, a primate (e.g., a monkey), a livestock animal (e.g., a horse, a cow, a sheep, a pig, or a goat), a companion animal (e.g., a dog, a cat), a laboratory test animal (e.g., a mouse, a rat, a guinea pig, a bird), an animal of veterinary significance, or an animal of economic significance.

As used herein, the terms "not responsive," and "non-responsive" to a treatment are used herein interchangeably to refer to a condition in which a patient or subject does not respond to a particular treatment or does not obtain a desired benefit after treatment for a particular disease. The terms "not responsive" and "non-responsive" include conditions in which a subject receives a treatment but does not experience a reduction in at least one symptom associated with the disease in the absence of the treatment. By way of example, a subject is not responsive to an anti-VEGF therapy if new blood vessels under the retinal of the patient continue to form despite receiving an anti-VEGF therapy or if a new blood vessel continues to grow while receiving the treatment.

As used herein, the term "non-responder" refers to a subject that is administered a therapeutic treatment for a particular disease but does not respond to or obtain benefit from the therapy. The term refers to subjects that do not experience a reduction in at least one symptom associates with the disease, e.g., a retinal angiogenic disease.

As used herein, "treating" or "treatment of" a condition, disease or disorder or symptoms associated with a condition, disease or disorder refers to an approach for obtaining beneficial or desired results, including clinical results. Beneficial or desired clinical results can include, but are not limited to, alleviation or amelioration of one or more symptoms or conditions, diminishment of extent of condition, disorder or disease, stabilization of the state of condition, disorder or disease, prevention of development of condition, disorder or disease, prevention of spread of condition, disorder or disease, delay or slowing of condition, disorder or disease progression, delay or slowing of condition, disorder or disease onset, amelioration or palliation of the condition, disorder or disease state, and remission, whether partial or total. "Treating" can also mean prolonging survival of a subject beyond that expected in the absence of treatment. "Treating" can also mean inhibiting the progression of the condition, disorder or disease, slowing the progression of the condition, disorder or disease temporarily, although in some instances, it involves halting the progression of the condition, disorder or disease permanently. As used herein the terms treatment, treat, or treating refers to a method of reducing the effects of one or more symptoms of a disease or condition characterized by expression of the protease or symptom of the disease or condition characterized by expression of the protease. Thus in the disclosed method, treatment can refer to a 10%, 20%, 30%, 40%, 50%, 60%, 70%, 80%, 90%, or 100% reduction in the severity of an established disease, condition, or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination.

The terms "polypeptide," "peptide," and "protein" are used interchangeably herein to include a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" includes naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs include compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" include chemical compounds that have a structure that is different from the general chemical structure of an amino acid, but that functions in a manner similar to a naturally occurring amino acid.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

As to amino acid sequences, one of skill will recognize that individual substitutions, deletions and/or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and/or alleles.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

The term "therapeutically effective amount" or "effective mount" includes an amount or quantity effective, at dosages and for periods of time necessary, to achieve the desired therapeutic or prophylactic result.

The term "administering" includes oral administration, topical contact, administration as a suppository, intravenous, intraperitoneal, intramuscular, intralesional, intrathecal, intranasal, or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. One skilled in the art will know of additional methods for administering a therapeutically effective amount of a fusion protein described herein.

Described herein are methods to treat subjects suffering from a number of retinal angiogenic diseases, e.g., age-related macular degeneration, retinopathy, or vascular occlusion. Retinopathy refers to a disease of the retina that results in impairment or loss of vision. Age-related macular degeneration ("AMD") is characterized by the invasion of new blood vessels into different-structures of the eye such as macular and retinal pigment epithelium. Vascular occlusion is a blockage in the retinal blood vessels, arteries or veins. Optionally, the subject has diabetic retinopathy, diabetic macular edema, central retinal vein occlusion, branch retinal vein occlusion, or corneal neovascularization. Subjects having one of these conditions may experience one or more of the following symptoms, visual field defects, difficulty to see textures and subtle changes in the environment, and difficulty to adjust for changing light levels, and impaired depth perception. Retinal angiogenic diseases can be diagnosed by a trained optometrist or other medical professional using methods well known in the art to examine the blood vessel formation under the retina, such as Dilated Eye Exam, Autofluorescence, Fundus Photography, Fluorescein Angiography, Optical Coherence Tomography (OCT), Tonometry, Fundoscopy or Ophthalmoscopy Optionally, the subject treated with the Angio-3 peptide was previously determined to be non-responsive to anti-angiogenesis therapies, e.g., anti-VEGF therapies. As used herein, anti-angiogenesis therapy refers to a therapy that blocks angiogenesis. As used herein, an anti-VEGF therapy refers to a therapy that blocks one or more VEGF function.

Non-limiting examples of anti-angiogenesis therapies include pegaptanib (Macugen™. by Pfizer), ranibizumab (Lucentis™ by Genentech) bevacizumab (Avastin™ by Genentech), carboxyamidotriazole, TNP-470, CM101, IFN-α, IL-12, platelet factor 4, suramin, SU5416, thrombospondin, VEGFR antagonists, angiostatic steroids+heparin, cartilage-derived angiogenesis inhibitory factor, matrix metallopreteinase inhibitors, angiostatin, endostatin, 2-methoxyestradiol, tecogalan, prolactin, alpha$_v$.beta$_3$ inhibitors, linomide., VEGF-Trap (by Regeneron Pharmaceuticals), Aminosterols (Evizion© by Genera Corp.), Cortisen (Retaane© by Alcon), tyrosine kinase inhibitors, anti-angiogenic siRNA, inhibitors of the complement system, gentherapeutic therapies (e.g. AdPEDF.11 by Genvec (Gaithersburg, Md.). Optionally, the anti-VEGF therapy is an anti-VEGF antibody, for example bevacizumab that are commercially available.

Optionally, the method of treating a retinal angiogenic disease comprises selecting a subject that has been diagnosed with a retinal angiogenic disease but is not responsive to anti-VEGF therapy. Administering the composition comprises an Angio-3 peptide disclosed herein, e.g., any one of SEQ ID Nos 1-4, or any combination thereof.

Angiostatin is a fragment of plasmin, which is a fragment of plasminogen. Plasminogen (UniProt No. P00747) contains five homologous repeats that form looped "kringle" structures held together by disulfide bonds. Plasminogen binds to fibrin through lysine binding sites located on the five kringle domains (k1 through k5) (Folkman et al, Nature Medicine, vol. 1, No. 1, pp. 27-31 1999). Each kringle domain is about 80 amino acid residues in length and different kringle domains are highly homologous to each other in amino acid sequences. Angio-3, is derived from the kringle domain k4 of plasminogen and is an angiogenesis inhibitor, i.e., it blocks the growth of new blood vessels, and has anti-inflammatory/anti-angiogenic activity. Angio-3 signaling pathway mediates the switch between a quiescent and an activated (i.e., angiogenic) endothelium. Unlike Vascular Endothelial Growth Factor (VEGF), which appears to uniformly promote angiogenesis, Angio-3 appears to have differing functions depending on endothelial cell context, with both cell-to-cell and cell-to-matrix contacts modulating the resulting signals.

It is believed that in many cases, patients having retinal angiogenic disease are not responsive to VEGF inhibitor therapy or become non-responsive after a period of time of treatment resulting in protection of VEGF-dependent endothelium. As described herein, delivering Angio-3 can disrupt the formation of new vessels and patients may be able to overcome resistance to anti-VEGF therapies. In particular, administering Angio-3 peptides can attenuate the retinal and/or choroidal angiogenesis and/or reduce lesion area of leakage in the eye caused by retinal angiogenesis.

The Angio-3 peptide that can be used to treat a retinal angiogenic disease can be the native Angio-3 peptide, which has a sequence of Thr Pro His Thr His Asn Arg Thr Pro Glu (SEQ ID NO: 1). The Angio-3 peptide can also be a peptide that contains modifications from SEQ ID NO:1 and yet retains the function of blocking angiogenesis. Some exemplar modifications to the peptide include sequence modifications and chemical modifications.

The polynucleotide sequences may encode Angio-3 polypeptides including those sequences with deletions, insertions, or substitutions of different nucleotides, which result in a polynucleotide encoding a polypeptide with at least one functional characteristic of the instant polypeptides, as described herein. Included within this definition are polymorphisms which may or may not be readily detectable using a particular oligonucleotide probe of the polynucleotide encoding the instant polypeptides, and improper or unexpected hybridization to allelic variants, with a locus other than the normal chromosomal locus for the polynucleotide sequence encoding the instant polypeptides.

Sequence alterations that do not change the amino acid sequence encoded by the polynucleotide are termed "silent" variations. Due to the degeneracy of the genetic code, with the exception of the codons ATG and TGG, encoding methionine and tryptophan, respectively, any of the possible codons for the same amino acid can be substituted by a variety of techniques, for example, site-directed mutagenesis, available in the art. Accordingly, any and all such variations of a sequence selected from the Sequence Listing are a feature of the instant disclosure.

In addition to silent variations, other conservative variations that alter one or a few amino acid residues in the Angio-3 peptide, can be made without altering the function of the polypeptide. For example, substitutions, deletions and insertions introduced into the sequences provided herein are also envisioned. Amino acid substitutions are typically of single residues; insertions usually will be on the order of about from 1 to 10 amino acid residues; and deletions will range about from 1 to 30 residues. In preferred embodiments, deletions or insertions are made in adjacent pairs, for example, a deletion of two residues or insertion of two residues. Substitutions, deletions, insertions or any combination thereof can be combined to arrive at a sequence. The mutations that are made in the polynucleotide encoding the peptide should not place the sequence out of the reading frame and should not create complementary regions that could produce secondary mRNA structure. Preferably, the polypeptide encoded by the DNA performs the desired function.

Conservative substitutions are those in which at least one residue in the amino acid sequence has been removed and a different residue inserted in its place. Such substitutions generally are made when it is desired to maintain the activity of the protein. Although all conservative amino acid substitutions (e.g., one basic amino acid substituted for another basic amino acid) in a polypeptide will not necessarily result in the polypeptide retaining the same activity as the native polypeptide, it is expected that many of these conservative mutations would result in the polypeptide retaining its activity.

Sequence variants of the Angio-3 peptides can be produced by modifying the respective wild-type sequences according to methods well-known to the skilled in the art. Such methods include, but not limited to, mutagenesis by PCR, which uses primers designed to contain desired changes; nested primers to mutate a target region; and inverse PCR, which amplifies a region of unknown sequence using primers orientated in the reverse direction. Many other mutation and evolution methods are also available and expected to be within the skill of a person of ordinary skill in the relevant art. Sequence variants of the Angio-3 peptide (SEQ ID NO: 1), as well as the Angio-3 peptide itself, can also be synthesized in the laboratory using methods well known in the art for peptide synthesis.

Accordingly, the disclosure also provides a scrambled Angio-3 peptide that has a sequence of Asn Thr Thr Glu Thr Pro His Pro His Arg (SEQ ID NO:2), which is used as a negative control for some of the studies disclosed herein.

Chemical or enzymatic alterations of expressed nucleic acids and polypeptides can be performed by standard methods. For example, sequences can be modified by the addition of lipids, sugars, peptides, organic or inorganic compounds, by the inclusion of modified nucleotides or amino acids, or the like. These methods can be used to modify any given sequence, or to modify any sequence produced by the various mutation and artificial evolution modification methods described herein and known to those of skill in the art.

The Angio-3 peptides disclosed herein may include natural amino acids, and, optionally, post-translational modifications thereof. However, in vitro peptide synthesis permits the use of modified and/or non-natural amino acids. A table of exemplary, but not limiting, modified and/or non-natural amino acids is provided herein below.

TABLE 1

Modified Amino Acids

| Abbr. | Amino Acid | Abbr. | Amino Acid |
|---|---|---|---|
| Aad | 2-Aminoadipic acid | EtAsn | N-Ethylasparagine |
| BAad | 3-Aminoadipic acid | Hyl | Hydroxylsine |
| BAla | beta-alanine, beta-Aminopropionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | Aile | allo-Isoleucine |
| Aib | 2-Aminoisobutyric acid | MeGly | N-Methylglycine, sarcosine |
| BAib | 3-Aminoisobutyric acid | MeIle | N-Methylisoleucine |
| Apm | 2-Aminopimelic acid | MeLys | 6-N-Methylly |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

Accordingly, the present disclosure provides for modifications of any given nucleic acid by mutation, chemical or enzymatic modification, or other available methods, as well as for the products produced by practicing such methods, e.g., using the sequences herein as a starting substrate for the various modification approaches.

Optionally, the modification to the native Angio-3 is to substitute arginine with a homoarginine. Homoarginine is the methylene homologue of L-arginine (Arg). It is an amino acid derivative and may increase nitric oxide availability and enhance endothelial function. Thus, optionally, the Angio-3 peptide that can be used to treat the retinal angiogenic diseases is Pep-N, which has a sequence of Thr Pro His Thr His Asn Xaa Thr Pro Glu, wherein Xaa is homoarginine (SEQ ID NO:3). Optionally, the Angio-3 peptide that can be used to treat the retinal angiogenic disease is Pep-Q, which has a sequence of Thr Pro His Thr His Gln Xaa Thr Pro Glu, wherein Xaa is homoarginine (SEQ ID NO:4).

The Angio-3 peptide may be prepared by methods known in the art. These methods include synthetic peptide chemistry, recombinant expression of the peptides of the disclosure using appropriate prokaryotic or eukaryotic host cells and expression systems or recombinant expression of the peptide as a feature of somatic gene transfer, i.e., expression as part of the administration regimen at the site of treatment.

Optionally, the peptide can be synthesized chemically using standard peptide synthesis techniques, e.g., solid-phase or solution-phase peptide synthesis. That is, the peptides disclosed as SEQ ID NOs:1-4 may be chemically synthesized, for example, on a solid support or in solution using compositions and methods well known in the art, see, e.g., Fields, G. B. (1997) Solid-Phase Peptide Synthesis. Academic Press, San Diego, incorporated by reference in its entirety herein. Such standard peptide-preparation techniques include, for example, solution synthesis or Merrifield-type solid phase synthesis, Boc (tert.butyloxycarbonyl), and the Fmoc (9-fluorenylmethyloxycarbonyl) strategies. Optionally, the peptides are synthesized by solid phase Fmoc chemistry using methods well known in the art (Ajikumar P K, Lakshminarayanan R, Ong B T, Valiyaveettil S, Kini R M. Biomacromolecules. 2003 September-October; 4(5):1321-6).

Provided herein is a pharmaceutical composition including a pharmaceutically acceptable excipient and an Angio-3 peptide. Also provided is a method of administering the composition for treating retinal angiogenic diseases, especially for subjects who are not responsive to anti-angiogenesis therapies, e.g. anti-VEGF therapies.

Pharmaceutical compositions or medicaments can be formulated by standard techniques using one or more physiologically acceptable carriers or excipients. Suitable pharmaceutical carriers are described herein and in, e.g., "Remington: The Science and Practice of Pharmacy, Twenty-First Edition" by E. W. Martin. The Angio-3 peptides and their physiologically acceptable salts and solvates can be formulated for administration by any suitable route, including, but not limited to, orally, topically, nasally, rectally, parenterally (e.g., intravenously, subcutaneously, intramuscularly, etc.), and combinations thereof. Optionally, the therapeutic agent is dissolved in a liquid, for example, water.

For oral administration, a pharmaceutical composition or a medicament disclosed herein can take the form of, e.g., a tablet or a capsule prepared by conventional means with a pharmaceutically acceptable excipient. Preferred are tablets and gelatin capsules comprising the active ingredient(s), together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate, (b) lubricants, e.g., silica, anhydrous colloidal silica, talcum, stearic acid, its magnesium or calcium salt (e.g., magnesium stearate or calcium stearate), metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulfate, and/or (f) absorbents, colorants, flavors and sweeteners. Optionally, the tablet contains a mixture of hydroxypropyl methylcellulose, polyethyleneglycol 6000 and titanium dioxide. Tablets may be either film coated or enteric coated according to methods known in the art.

Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

For topical administration, the compositions of the present disclosure can be in the form of emulsions, lotions, gels, creams, jellies, solutions, suspensions, ointments, and transdermal patches. For delivery by inhalation, the composition can be delivered as a dry powder or in liquid form via a nebulizer. For parenteral administration, the compositions can be in the form of sterile injectable solutions and sterile packaged powders. Preferably, injectable solutions are formulated at a pH of about 4.5 to about 7.5.

The compositions can also be provided in a lyophilized form. Such compositions may include a buffer, e.g., bicarbonate, for reconstitution prior to administration, or the buffer may be included in the lyophilized composition for reconstitution with, e.g., water. The lyophilized composition may further comprise a suitable vasoconstrictor, e.g., epinephrine. The lyophilized composition can be provided in a syringe, optionally packaged in combination with the buffer for reconstitution, such that the reconstituted composition can be immediately administered to a patient.

The compounds can be encapsulated in a controlled drug-delivery system such as a pressure controlled delivery capsule, a colon targeted delivery system, a osmotic controlled drug delivery system, and the like. The pressure controlled delivery capsule can contain an ethylcellulose membrane. The colon target delivery system can contain a tablet core containing lactulose which is over coated with an acid soluble material, e.g., Eudragit E©, and then overcoated with an enteric material, e.g., Eudragit L©. The osmotic controlled drug delivery system can be a single or more osmotic unit encapsulated with a hard gelatin capsule (e.g., capsule osmotic pump; commercially available from, e.g., Alzet, Cupertino, Calif.). Typically, the osmotic unit contains an osmotic push layer and a drug layer, both surrounded by a semipermeable membrane.

Pharmaceutical compositions or medicaments can be administered to a subject at a therapeutically effective dose to treat a retinal angiogenic disease as described herein. Optionally, the pharmaceutical composition or medicament is administered to a subject in an amount sufficient to elicit an effective therapeutic response in the subject.

Typically, a dosage of the active compounds is a dosage that is sufficient to achieve the desired effect. Optimal dosing schedules can be calculated from measurements of agent accumulation in the body of a subject. Generally, administered dosages can vary depending on a number of factors, including, but not limited to, the subject's body weight, age, individual condition, surface area or volume of the area to be contacted, and/or on the routes of administration. The size of the dose will also be determined by the existence, nature, and extent of any adverse effects that accompany the administration of a particular compound in a particular subject. Preferably, the smallest dose and concentration required to produce the desired result should be used. Dosage should be appropriately adjusted for children, the elderly, debilitated patients, and patients with cardiac and/or liver disease. Further guidance can be obtained from studies known in the art using experimental animal models for evaluating dosage.

Optionally, the composition is administered by intravenous injection. A unit dosage for intravenous administration to an individual (e.g., human) may contain 2-50 mg of active ingredient per 1 kg of body weight, which is also referred to as 2-50 mg/kg Bwt. For example, for a patient of about 50 kg, the unit dosage may contain 100 mg-2,500 mg of the active ingredient of Angio-3 peptide. Optionally, the unit dosage is 2-50 mg/kg Bwt., e.g., 10-50 mg/kg Bwt., 25-45 mg/kg Bwt., or 20 to 40 mg/kg Bwt. The volume of the unit dosage varies, Optionally, the volume is within a range of 10-200 µl, e.g., 40-150 µl, 100-200 µl, 120-150 µl, or 50-160 µl.

Optionally, the composition is administered by intravitreal injection. Typically, a unit dosage for intravitreal administration may contain 0.1 µg/kg Bwt.-2 mg/kg Bwt., e.g., 0.5 µg/kg Bwt.-2 mg/kg Bwt., 1-2 mg/kg Bwt., or 1 to 1.5 mg/kg of the angio-3 peptide. The volume of the unit dosage may vary, for example, it may be a volume within the range of 10-80 µl, e.g., 20-60 µl, or 30-50 µl.

Optionally, the composition is administered orally. Typically, a unit dosage for oral administration may contain 2 mg/kg Bwt.-10 mg/kg Bwt., e.g., 2 µg/kg Bwt.-8 mg/kg Bwt., 5-10 mg/kg Bwt., or 4 to 6 mg/kg of the Angio-3 peptide.

The dosage of a composition can be monitored and adjusted throughout administration period, depending on severity of symptoms, frequency of recurrence, and/or the physiological response to the therapeutic regimen. Those of skill in the art commonly engage in such adjustments in therapeutic regimens.

To achieve the desired therapeutic effect, the compositions may be administered for multiple days at the therapeutically effective dose. Thus, therapeutically effective administration of the compositions of the disclosure to treat a pertinent condition or disease described herein in a subject requires periodic (e.g., daily) administration that continues for a period ranging from four weeks or two years or longer. A therapeutically beneficial effect can be achieved if the agents are administered daily, or at a frequency that is enough to maintain a therapeutically effective concentration of the agents in the subject. For example, one can administer the agents every day, every other day, or, if higher dose ranges are employed and tolerated by the subject, e.g., twice a week.

The duration of treatment with Angio-3 peptides to treat patients vary according to severity of the condition in a subject and the subject's response to Angio-3. Treatment with the Angio-3 in accordance with the disclosure thus may last for as long as five, six, eight, ten weeks or even longer. Optionally, the composition can be administered for a period of about 4 weeks to 2 years, more typically about 6 weeks to about 1 year, most typically about 6 months to 1 year. Suitable periods of administration also include about 18 weeks to 1 year, 9 to 16 weeks, 16 to 24 weeks, 16 to 32 weeks, 24 to 32 weeks, 24 to 48 weeks, 32 to 48 weeks, 32 to 52 weeks, 48 to 52 weeks, 48 to 64 weeks, 52 to 64 weeks, 52 to 72 weeks, 64 to 72 weeks, 64 to 80 weeks, 72 to 80 weeks, 72 to 88 weeks, 80 to 88 weeks, 80 to 96 weeks, 88 to 96 weeks, and 96 to 104 weeks. Suitable periods of administration also include 5, 6, 7, 8, 9, 10, 11, 12, 13, 14, 15, 16, 17, 18, 19, 20, 24, 25, 30, 32, 35, 40, 45, 48, and 50 weeks. Generally administration of the composition should be continued until clinically significant improvement of the condition is observed.

Optionally, administration of the composition comprising the Angio-3 peptide is not continuous and can be stopped for one or more periods of time, followed by one or more periods of time where administration resumes. Suitable periods where administration stops include 1 to 9 months, 1 to 6 months, 9 to 16 weeks, 16 to 24 weeks, 2 to 32 weeks, 24 to 32 weeks, 24 to 48 weeks, 32 to 48 days, 32 to 52 days, 48 to 52 days, 48 to 64 days, 52 to 64 days, 52 to 72 days, 64 to 72 days, 64 to 80 days, 72 to 80 days, 72 to 88 days, 80 to 88 days, 80 to 96 days, 88 to 96 days, and 96 to 100 days. Suitable periods where administration stops also include 5, 6, 7, 8, 9, 10, 11, 12, 13, 14, 15, 16, 17, 18, 19, 20, 24, 25, 30, 32, 35, 40, 45, 48 50, 52, 55, 60, 64, 65, 68, 70, 72, 75, 80, 85, 88 90, 95, 96, and 100 days.

Optionally, the composition is administered orally to patients once, twice, or more times per day. Optionally, the daily oral administration of the composition comprising the Angio-3 peptide is administered for at least two (2) weeks, at least three (3) weeks, or for 1-2 weeks during a time interval. In some cases, the interval is 3, 4, 6, 7, or 8 months. In general, administration of Angio-3 is continued until the desired therapeutic benefit is achieved. The entire treatment period, from the delivering the first dose to the delivery of the last dose, may be 6, 7, 8, 9, 10, 11, 12, 13, 14, 15, 16, 17, 18, 19, 20, 24, 25, 30, 32 months. Optionally, the entire treatment period lasts 6 to 10 months, 12 to 24 months, 6 to 32 weeks, 24 to 32 weeks, 24 to 48 weeks, 32 to 48 months, or 32 to 52 months.

Optionally, the composition is delivered either intravenously or intravitreally at least once, twice, or more every 24 weeks, every 20 weeks, every 15 weeks, every 12 weeks, every 10 weeks, or every 4 weeks. Optionally, the composition is delivered either intravenously or intravitreally once every 4 to 10 weeks.

The Angio-3 composition disclosed herein can be used in combination with other active agents known to be useful for treating a retinal angiogenic disease, or with adjunctive agents that may not be effective alone, but may contribute to the efficacy of atropine. The Angio-3 composition can also be used in conjunction with laser therapy or surgery to treat a retinal angiogenic disease.

An Angio-3 composition disclosed herein can be placed in an appropriate container, such as bottles or droppers, and labeled for treatment of an indicated condition. For administration of the atropine composition, such labeling would include, e.g., instructions concerning the amount, frequency and method of administration.

Patients are monitored by eye examinations at the beginning of the treatment and during periodic examinations during and/or after treatment. In some cases, the patients are monitored, e.g., every four, five, six months, seven, or eight months during and/or after the treatment period. Methods for determining the progression of retinal angiogenic disease are well known, for example through Colour Fundus photography ("CFP"), Fundus Fluorescein Angiography ("FFA"), Optical coherence tomography ("OCT") an visual aquity test. The response to treatment is assessed by both qualitative and quantitative analysis via clinical scoring system.

EXAMPLES

The following examples are for illustrative purposes only and should not be interpreted as limitations. There are a variety of alternative techniques and procedures available to those of skill in the art, which would similarly permit one to successfully perform the provided methods.

Example 1. Efficacy of Angio-3 in Non-Human Primate (NHP) Laser-Induced CNV

This Pilot efficacy study was conducted on NHP laser induced choroidal neovascularization ("CNV") model. Four monkeys were used for this pilot study and each animal was undergone eye examination procedures. Animals were sedated with ketamine intramuscularly (10-20 mg/kg) and Medetomidine (0.02 mg/kg; IM). Topical anaesthesia (1-2 drops of 1% xylocaine) was applied to reduce the discomfort of the eyes. Pupils of non-human primates were dilated with 2.5% phenylephrine hydrochloride and 1% tropicamide drops for the ocular imaging procedures.

Laser Photocoagulation (Laser-Induced CNV):

Laser photocoagulation was performed on both eyes of the animals to create a model for CNV as previously described (Lai C M et al., 2005). Briefly, nine laser burns was delivered around the macula of each eye in the manner of a grid with a protocol of 500-800 mW power intensity, 50-micron spot size, and 0.1-s duration. The distance from each laser spot to the central fovea was maintained at 0.5 to 1 disc diameter size. Care was taken to avoid damaging the fovea.

Animals was observed twice daily for signs of potential adverse events, and once daily for qualitative assessment of food consumption. The body weights of the animals were recorded on the day of transfer, at the time of animal selection for laser injury and on the day of dose administration, and every week throughout the remainder of the study.

Intravitreal Injection:

After the animal being anesthetized, the eyes were locally anesthetized by putting a drop of xylocaine in the conjunctival sac. A 5% povidone iodine solution was placed in the conjunctival sac. A self-retaining eyelid speculum was placed in the eye. Caliper was used to measure and mark a location at 2 mm behind the limbus. Forceps was also be used to stabilize the eye and the intravitreal injection was performed using a 30-gauge needle. The tested compounds (2 mg in 50 µl) were administered single IVT injection into both eyes on day 15 (14 days after laser injury). Daily cage-side observations were performed on all animals to monitor for clinical signs of poor health, including any ocular abnormalities.

Colour Fundus Photography (CFP) and Fundus Fluorescein Angiography (FFA):

Fundus photography was carried out on both eyes at pre-laser and day 14 post-laser and day 29 post laser (2 weeks after treatment). For photography the pupils were dilated as mentioned above and imaged with a fundus camera (TopCon Corp., Tokyo, Japan). The fundus photographs were used to detect any changes in the retina such as inflammation and pigmentation.

FFA was performed on both eyes by intravenous injection of 10% sodium fluorescein dye (0. ml/kg body wt). The fundus images were taken between 10 s and 15 min after dye injection. FFA images were assessed and graded according to standardized system:

Grade 1—No hyperfluorescence—No leak
Grade 2—Hyperfluorescence—No leak
Grade 3—Hyperfluorescence—Late leak
Grade 4—Bright Hyperfluorescence with Late Leak Beyond Spot Optical Coherence Tomography (OCT):

OCT was carried out on both eyes at pre-laser and day 14 post-laser and day 29 post laser (2 weeks after treatment).

Euthanasia and Tissue Collection:

Animals were sacrificed on Day 30. Eye, blood, ocular fluids and internal organs were collected for further analysis.

Animals were sacrificed on the proposed day (day 30) and the upper body was perfused through the aorta (descending clamped) with half-strength Karnovsky fixative. The eyes were removed, postfixes for 2 to 3 days in half-strength Karnovsky fixative, and then stored in formalin until processed. Strips of tissue containing 1 or 2 lesion sites were embedded in plastic. Sections 2 µm thick were taken at 30-µm steps through the middle of each lesion. The sections were stained with toluidine blue, and the sample with the most robust lesion was designated as the central cut. This section was then evaluated by an observer masked to the treatment condition.

A tissue proliferation score was calculated for each lesion based on 3 criteria: the size of the spindle cell proliferative lesion, the extent of new blood vessel proliferation in the subretinal space, and the elevation of the retina above the choriocapillaris. Each measure was graded from 0 to 3, with 0 indicating not present. The total tissue proliferation score comprises the sum of each of the described measures for each laser lesion site.

Results

Figure 1A:
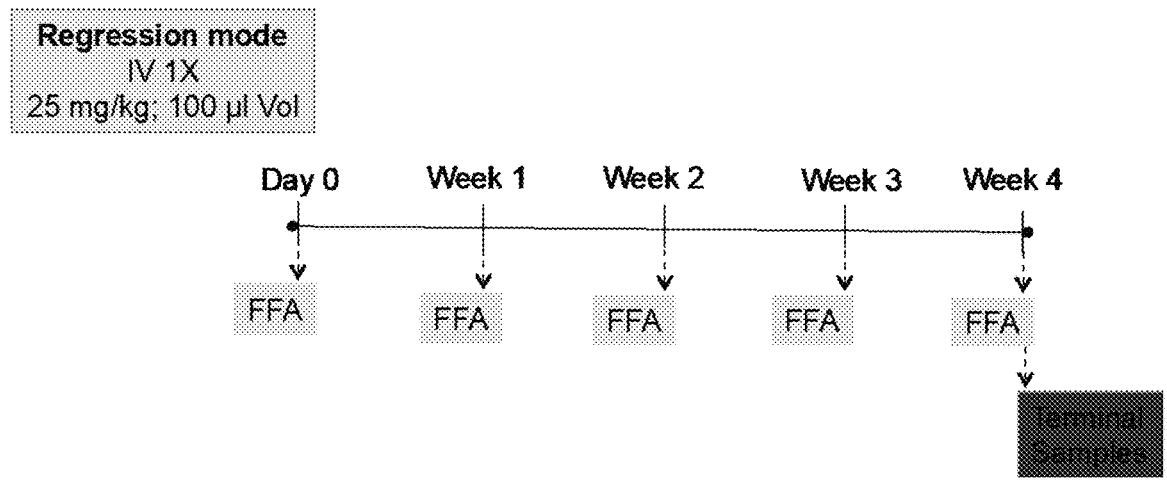
FIGS. 1A, 1B, 1C and 1D show the efficacy of a single IV dose of angio-3 in attenuating the retinal angiogenesis in KIMBA mice, which have over expression of human VEGF (KIMBA-hVEGF Transgenic).
Figure 1B:
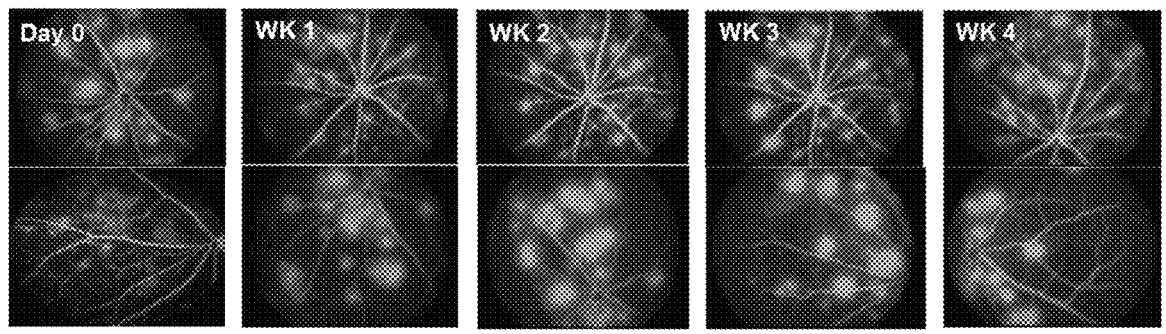
Figure 1B:
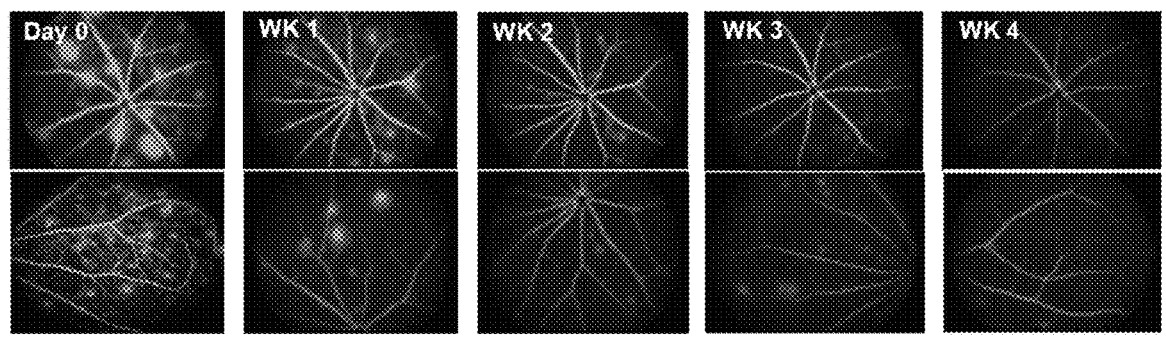
Figure 1C:
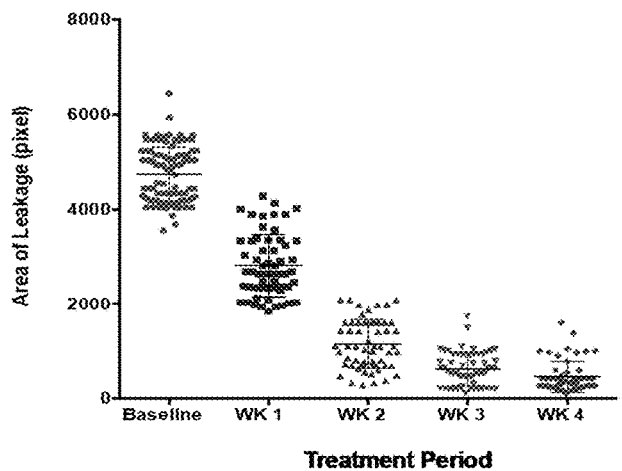
Figure 1C:
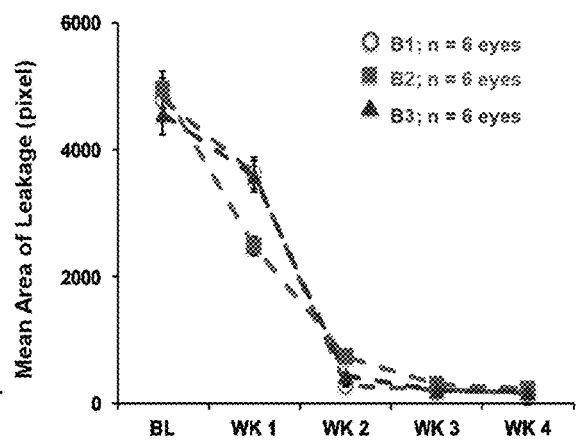
Figure 1D:
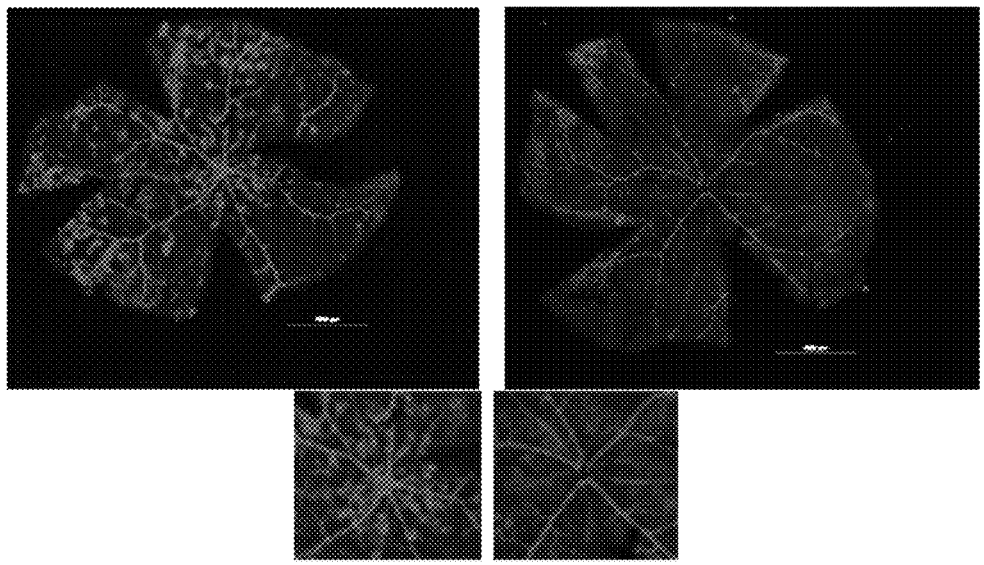
Figure 2A:
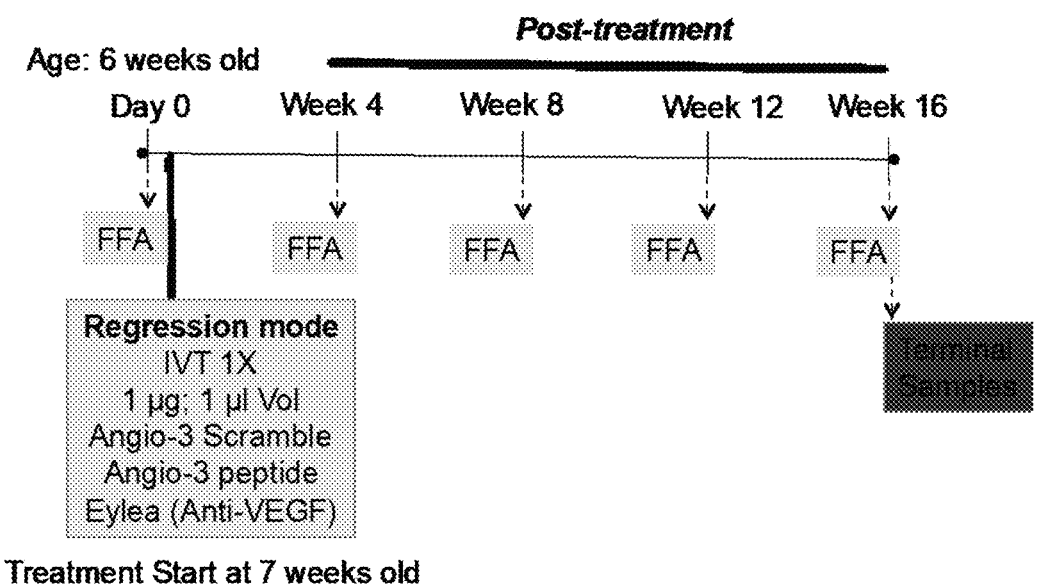
Figure 2B:
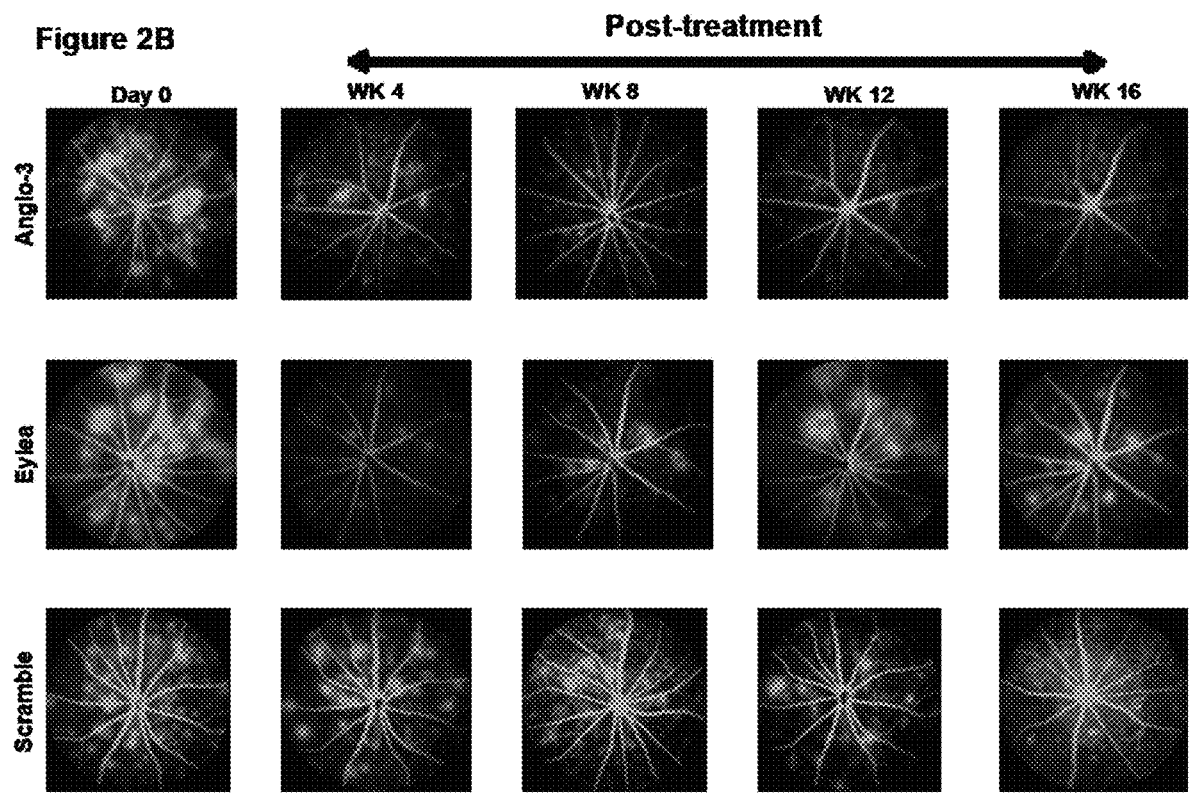
Figure 2C:
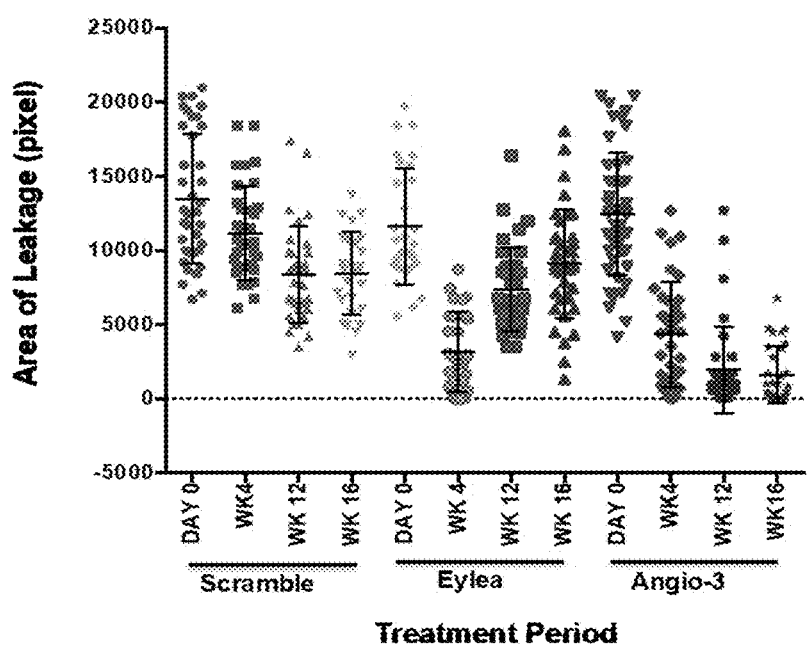
Figure 3A:
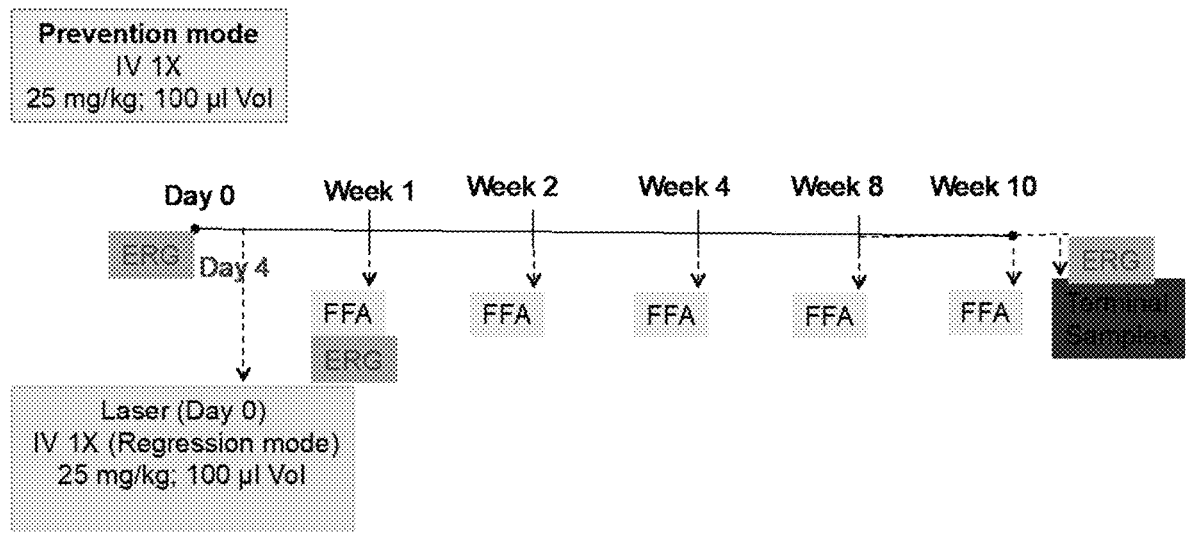
FIG. 3A is a schematic of the experimental design on the efficacy of Angio-3 in a laser-induced choroidal neovascularization (CNV) model in mice (B6J WT mice).
Figure 3B:
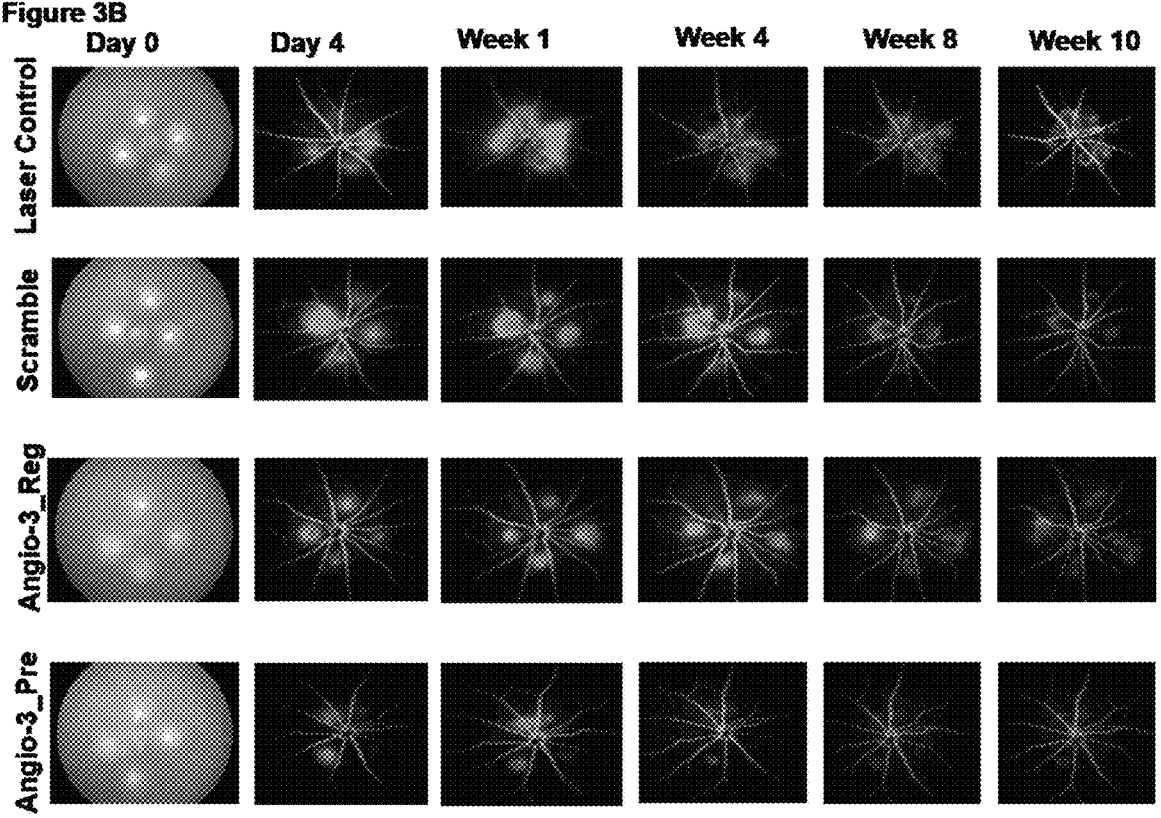
FIG. 3B are FFA images of baseline and at different time points post treatment. IV single injection of 100 μL of Angio-3 (25 mg/Kg Bwt) was given at Day 0 (prevention mode) and 4 days after laser (regression mode) and followed for 10 weeks.
Figure 3E:
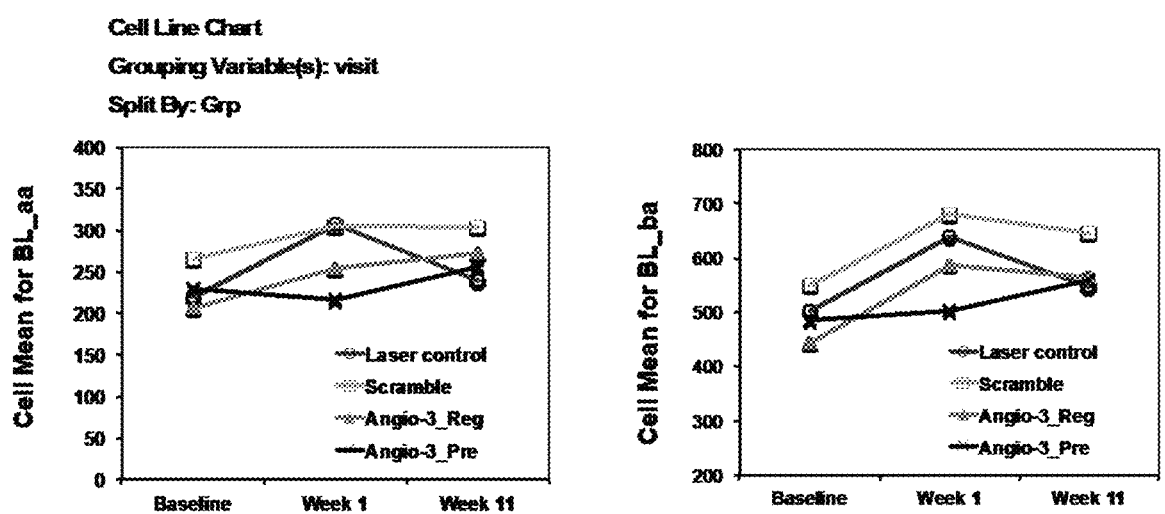
FIG. 3E is a graph of the result of the Retinal Function Test that measures ERG changes in Angio-3 treated and control. The a- and b-wave amplitude of the Angio-3 treated group, however, was similar to that of baseline values after weak 1.
Figure 4A:
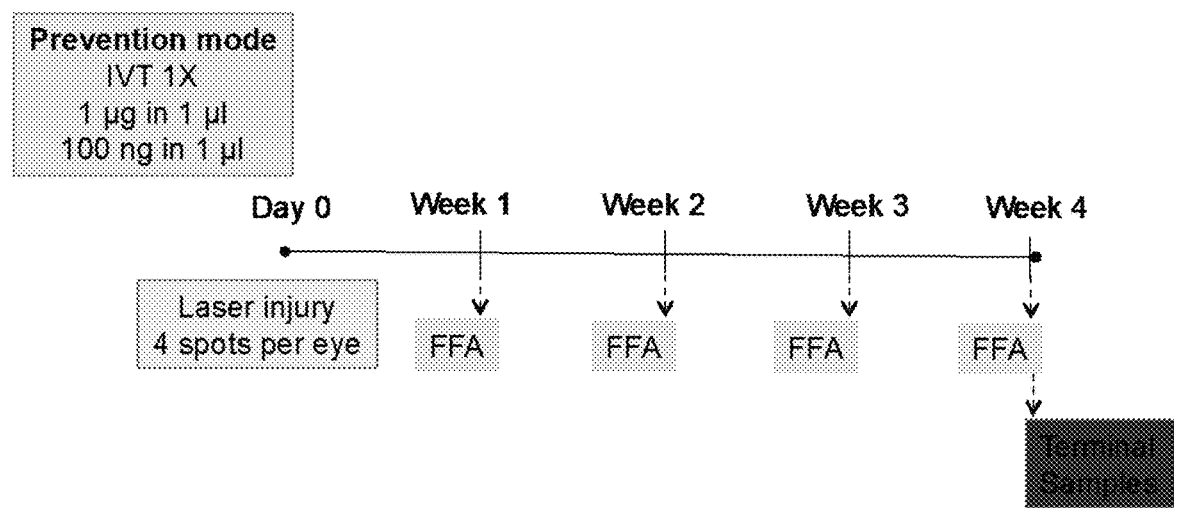
FIG. 4A is a schematic of the experimental design on the efficacy of Angio-3 by IVT administration.
Figure 5A:
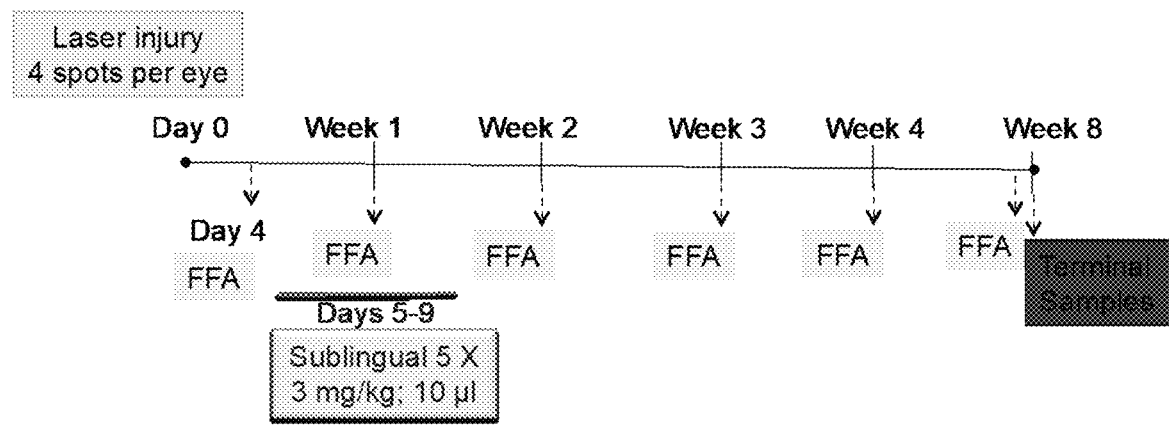
FIG. 5A is a schematic of the experimental design on the efficacy of Angio-3 in a laser-induced CNV model by sub-lingual route.
Figure 5B:
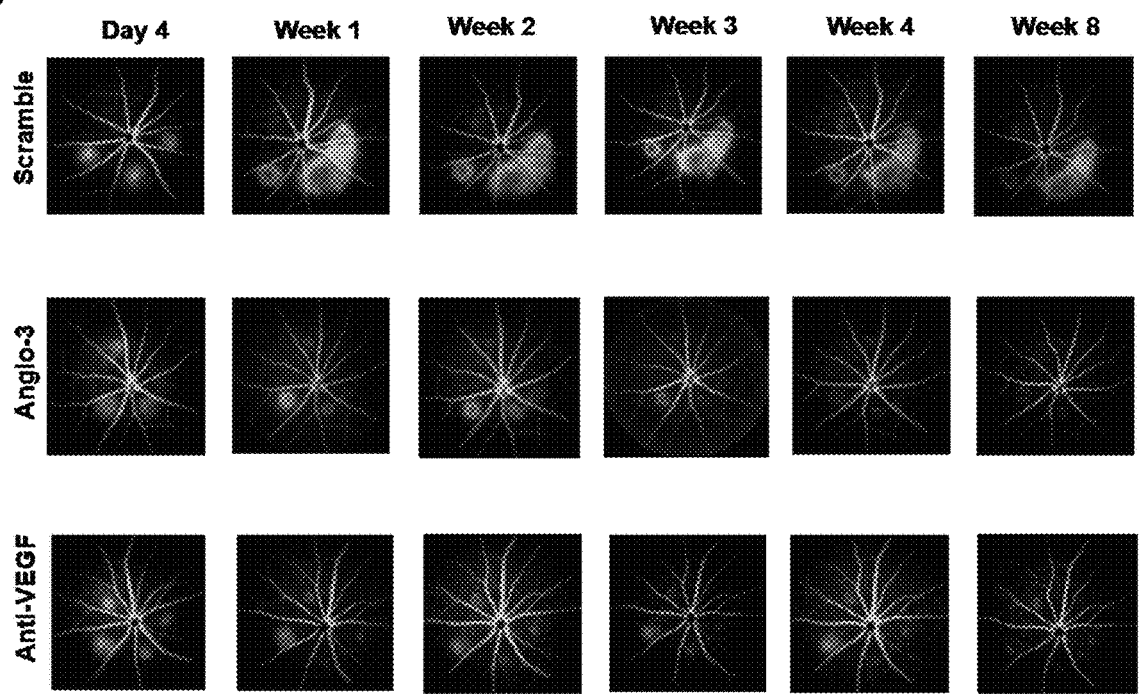
FIG. 5B are images showing Angio-3 significantly reduced angiogenesis than murine anti-VEGF or scrambled peptide in laser-induced mice CNV model via sub-lingual route.
Figure 5C:
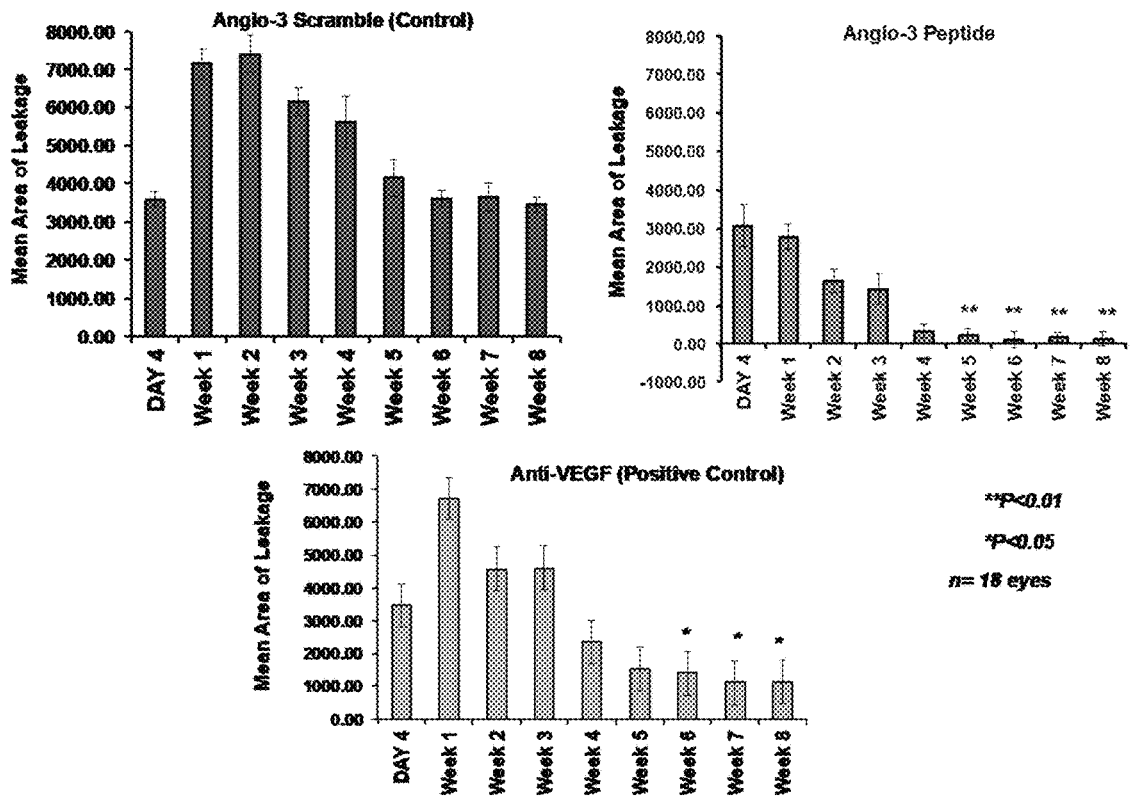
FIG. 5C is a graph of the mean area of leakage by groups and FIG. 5D shows the mean area of leakage of all batches for each group. n=6 eyes per batch; n=3 batches. Values are expressed as means s.e.m., **P<0.01, *P<0.05, student's t-test.
Figure 5D:
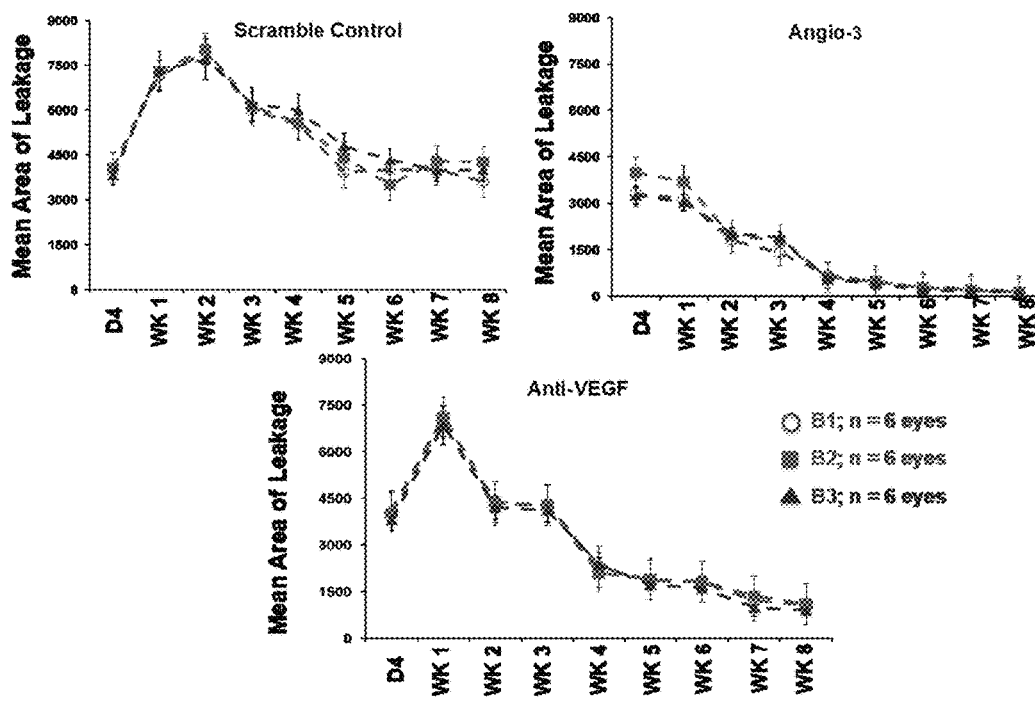
Figure 6A:
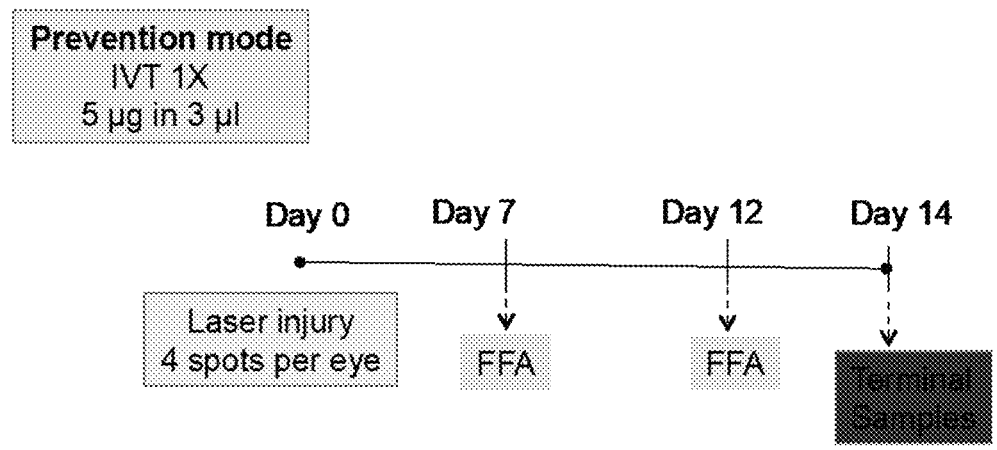
FIG. 6A is a schematic of the experimental design on the efficacy of Angio-3 in a laser-induced CNV model by IVT route in a prevention mode.
Figure 6B:
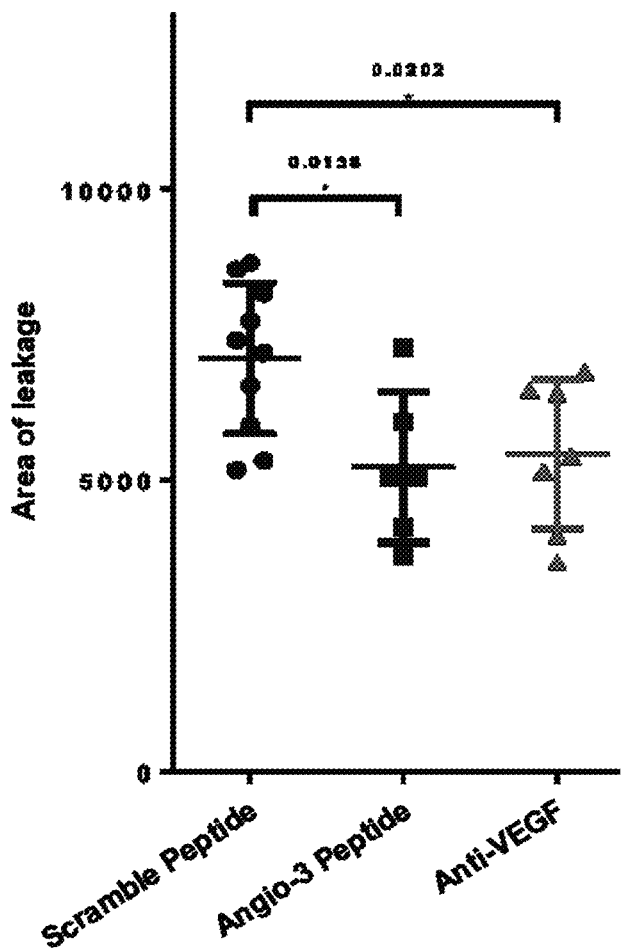
FIG. 6B are graphs showing a single dose Angio-3 significantly reduced angiogenesis as compared to Eylea (anti-VEGF) in laser-induced rat CNV model via IVT route. n=10 rats per group; Values are expressed as means s.e.m., n=3 independent experiment, **P<0.01, *P<0.05, student's t-test.

Our study result showed that Angio-3 peptide significantly attenuates the retinal angiogenesis in KIMBA mice (FIG. 1A-D). Eylea (positive control) is only effective for 4 weeks post treatment when commenced treatment at 6 weeks of old Kimba mice via IVT. However, Angio-3 (test peptide) is effective for up to 16 weeks post treatment (FIG. 2A-D). This data indicates the long duration of Angio-3 efficacy in mice model Laser-induced mice model study demonstrated that Angio-3 peptide significantly attenuates the retinal and choroidal angiogenesis via I/V route by single dose till week 10 (FIGS. 3A-C). The systemic route did not affect the natural wound healing process, menstrual cycle and behavioural change, which shows that Angio-3 is safe to given via IV route. Angio-3 also significantly attenuates the retinal and choroidal angiogenesis than anti-VEGF via IVT route (FIGS. 4A-B). Angio-3 also shows significantly attenuates the retinal and choroidal angiog than anti-VEGF via sub-lingual route (FIG. 5A-C). In addition, our study shows that Angio-3 could be a potential long acting anti-angiogenic for retinal and choroidal angiogenesis diseases (FIGS. 3 and 4). In addition, we also determine the retinal function with and without Angio-3 treatment. There was no significant difference in retinal function noticed in all groups. However, a and b-wave response was lower than baseline at week 26 that was due to normal ageing process (FIG. 3D). The optimal dose was found in rat CNV model study. Angio-3 significantly attenuates the retinal and choroidal angiogenesis than anti-VEGF via IVT route at 5 µg dose (FIGS. 6A-B).

Figure 7A:
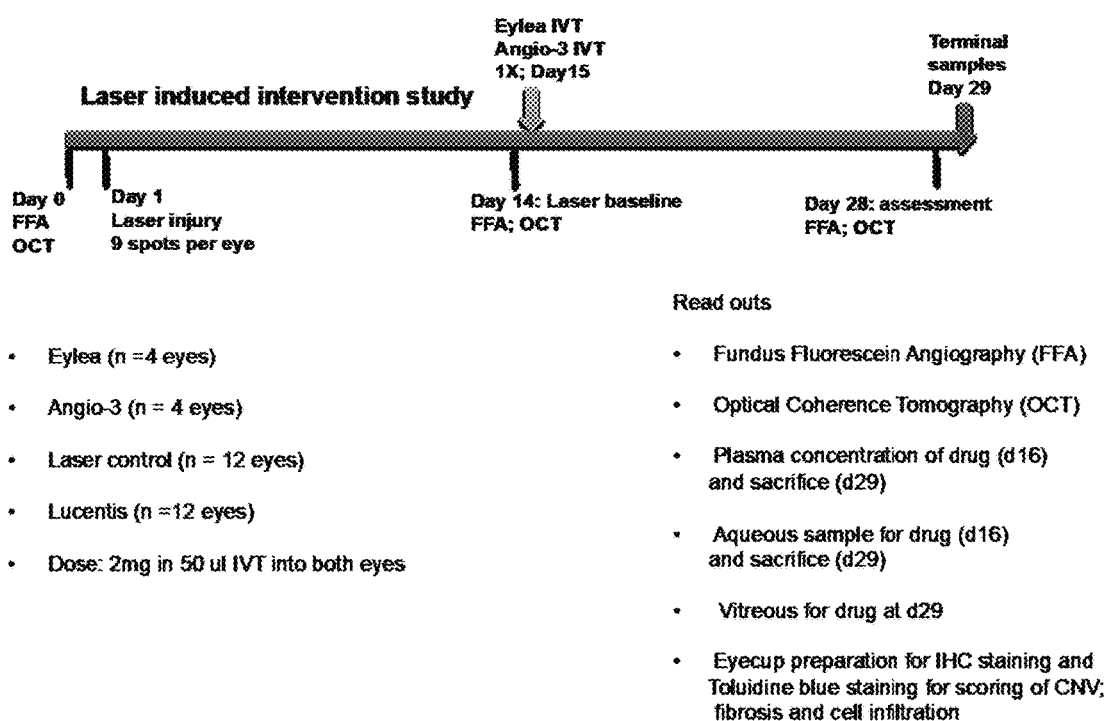
FIG. 7A is a schematic of the study design on the efficacy of Angio-3 in a monkey model of laser-induced CNV.
Figure 7A:
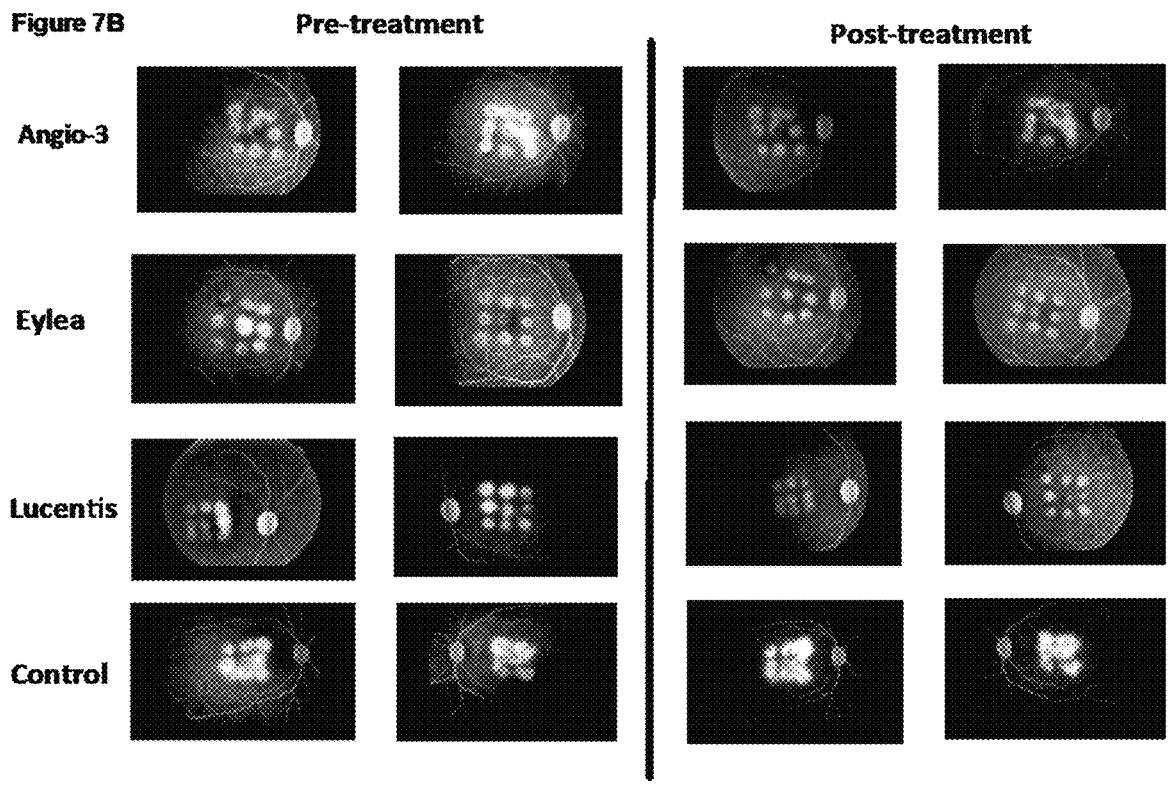
Figure 8:
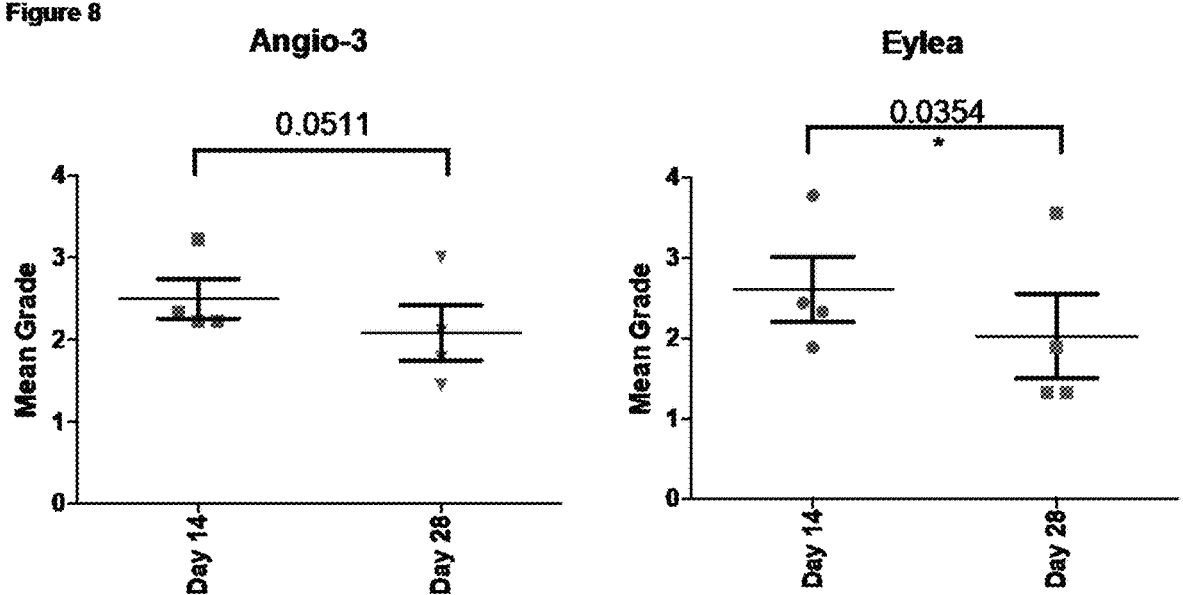
FIG. 8 is a graph showing severity of grade and percentage of grades in monkeys treated as described in FIG. 7. Following a single IVT dose of Angio-3, Eylea and Lucentis®, the test article formulations were well tolerated and all animals appeared generally healthy. A few animals developed intraocular inflammation, mostly short-lived, in the study eye after intravitreal injection in all groups. In this intervention study, no change in lesion severity was observed for the vehicle control and the change in lesion severity was significantly different for all treatments compared with vehicle control.
Figure 8:
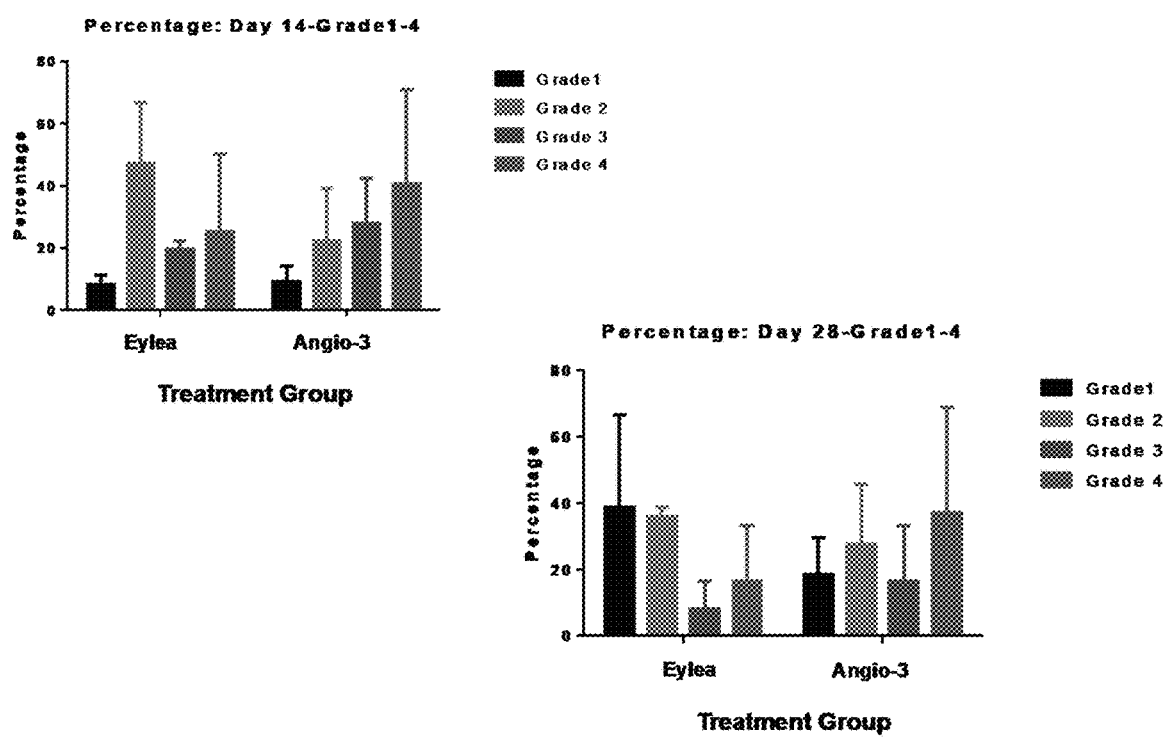
Figure 9:
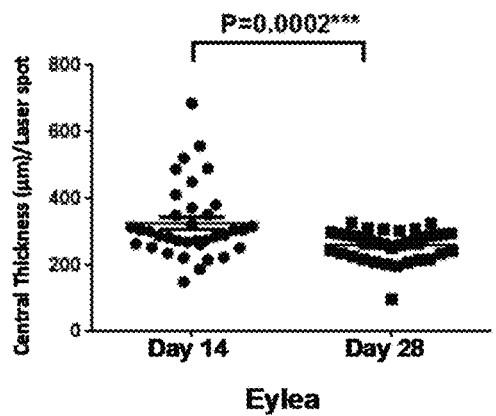
FIG. 9 is a graph showing results of laser spot area thickness and volume in monkeys before and after administration of Eylea or Angio-3. The amount of Angio-3 or Eyelea is the same as described in FIG. 7. The laser spot area was significantly reduced after treatment as compared to pre-treatment in both groups.
Figure 9:
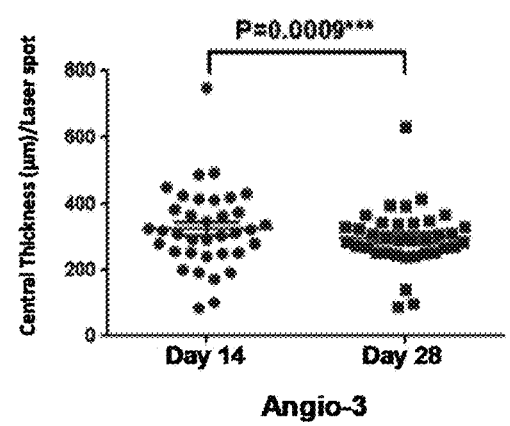
Figure 9:
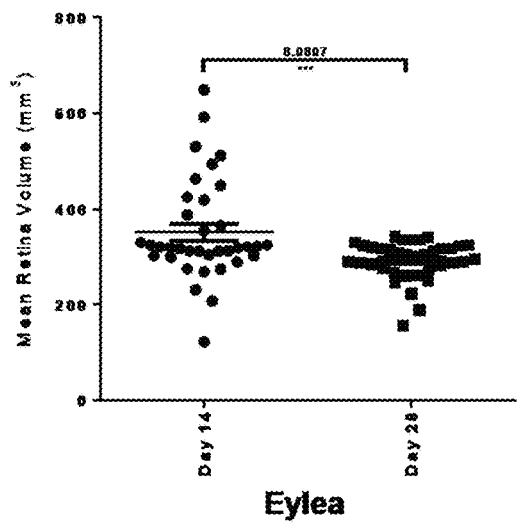
Figure 9:
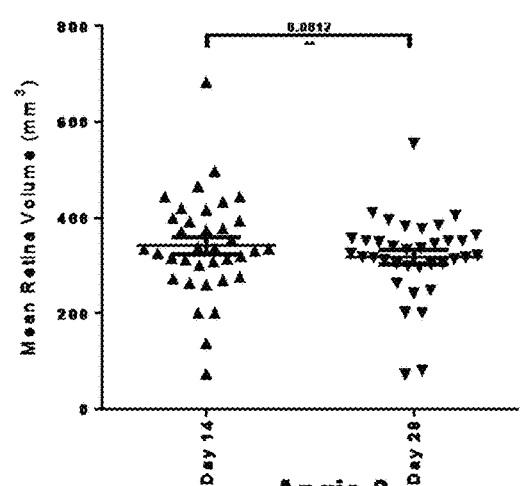

This NHP pilot study shows that 2 mg in 50 µl dose of SIPRAD-0276 (Angio-3) was well tolerated via IVT and no signs of inflammation found. This dose showed that same efficacy as compared to 2 mg in 50 µl of Eylea (FIGS. 7A-C). However, this was not superior to Lucentis. Severity of lesion grade was significantly reduced as compared to vehicle control (FIG. 8). Lesion area of volume and thickness was significantly reduced post treatment (FIG. 9).

Figure 10:
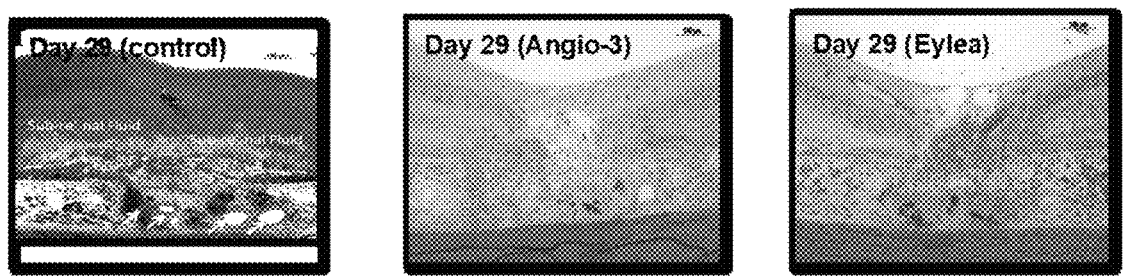
FIG. 10 are images of araldite retina sections stained with toluidine blue (Magnification 20×). The eyes were removed, postfixed for 2 to 3 days in half-strength Karnovsky fixative, and then stored in formalin until processed. Strips of tissue containing 1 or 2 lesion sites were embedded in plastic. Sections 2 μm thick were taken at 30-μm steps through the middle of each lesion. The sections were stained with toluidine blue, and the sample with the most robust lesion was designated as the central cut. This section was then evaluated by an observer (R.R.D.) masked to the treatment condition. A tissue proliferation score were calculated for each lesion based on 3 criteria: the size of the spindle cell proliferative lesion, the extent of new blood vessel proliferation in the subretinal space, and the elevation of the retina above the choriocapillaris. Vehicle treated (control) sections are thicker and more vascular compared with the drug-treated eyes.

Based on histopathological analysis (FIG. 10), vehicle treated (control) sections are thicker and more vascular compared with the drug-treated eyes. Control sections showed more choroidal fibroplasia (red arrows), increased retinal thickness, more choroidal neovascularization (white arrows), multiple vessels extending once or twice the retinal thickness and retinal elevation as compared to drug-treated eyes. In this figure, the degree of vessel leakiness was associated with morphological changes in the retina at the site of laser injury. A distorted retinal architecture was apparent if a laser spot was strongly leaky at the day 29 time point, as revealed by thickening of the retina, massive fibrosis, and edematous vacuoles. Control sections are thicker and more vascular compared with the drug-treated eyes.

Angio-3 peptide also suppresses VEGF-induced endothelial cell vascular permeability (VP) in vitro including VEGF-induced VP of human retinal endothelial cells (HRECs). It also inhibits dermal vascular permeability in mice. It is envisioned that Angio-3 would also inhibit VP in the eye and this function contribute to Angio-3's function to suppress vascular leakage in the Kimba mice eye.

Conclusions

Laser-induced CNV in NHP is the gold-standard for drug discovery and development of RAD. This pilot study result confirms that Angio-3 shows efficacy as close to Eylea and this peptide would be benefit to anti-angiogenesis therapy non-responders.

This peptide can be administered as intravenous or oral or via IVT application for prevention or treatment of retinal angiogenic diseases.

The animal model study result confirms that Angio-3 has a long-term anti-VEGF effect, therefore has potentially greater benefit than current drug on the market.

As compared to current drugs for the same disease condition, we can produce even higher concentration (will find out tolerable highest dose from next study) for low cost as this peptide has only 10 amino acid residues.

Example 2. Efficacy of Angio-3 Peptide Against Comparator Murine Anti-VEGF on Retinal Angiogenic Diseases Animals:

Aim of this study was to evaluate the efficacy of Angio-3 peptide against comparator murine anti-VEGF on retinal angiogenic diseases. C57BL/6J wild type (WT) mice were purchased from InVivos (Singapore). Kimba transgenic mice breeders were purchased from The Lions Eye Institute, Perth, Australia. Brown Norway rats were purchased from Charles & River Laboratories. In our facility, KIMBA mice breeding colony was maintained and mice were bred for the present study. Animals were housed on a 12 h light/12 h dark cycle with food and water provided ad libitum. Handling and care of all animals were performed according to the guidelines approved by SingHealth Institutional Animal Care and Use Committee (IACUC], Singapore, and is conducted in accordance with the Association for Research in Vision and Ophthalmology (ARVO) recommendations for animal experimentation.

Animal Model

The Kimba mouse (n=39) is a transgenic mouse model for retinal neovascularisation, generated through photoreceptor-specific over expression of human vascular endothelial growth factor (hVEGF) protein. The retinal neovascular changes include increased permeability, pericyte and endothelial cell loss, vessel tortuosity, leukostasis and capillary blockage, dropout and haemorrhage. The Kimba mouse model is particularly suitable for testing anti-angiogeneic molecules designed to target hVEGF.

Laser induced choridal neo-vascularization (CNV) in C57/BL6J (B6J) wild type mice (n=90).

Laser induced choridal neo-vascularization (CNV) in Brown-Norway rats (n=30).

Treatment Mode

Kimba mice received 25 mg/kg Bwt Angio-3 via intravenous (IV) route, single injection of 100 µl volume.

Angio-3 was also injected via intravitreal (IVT) route in Kimba mice, single injection of 1 µl volume at 1 µg dose.

In B6J mice, single injection of 100 µl volume at 25 mg/kg Bwt concentration Angio-3 was injected via intravenous (i/v) route and this was tested in both Preventive mode (before laser) and Regression mode (4 days after laser).

In B6J mice, 10 µl volume at 3 mg/kg Bwt concentration Angio-3; 10 µl volume at 3 mg/kg Bwt concentration Angio-3 scramble and 10 ul volume at 0.1 mg/kg Bwt concentration anti-VEGF was given via sub-lingual (oral) route and this was tested in Regression mode (4 days after laser) and continued for 5 days (single dose per day).

Angio-3 was also injected via intravitreal (IVT) route, single injection of 1 µl volume at 2 different doses; 1 µg (High dose) and 100 ng (Low dose).

This was further evaluated in Brown-Norway rats to identify the optimal dose of Angio-3. Rats received 5 µg (High dose) and 1 µg (Low dose) of Angio-3 via IVT route, single injection of 3 µl volume.

Laser Induced CNV:

4 laser photocoagulation sites were placed concentrically around the optic disc of both eyes to induce CNVs. A diode laser (810 nm) was used with a relative potency scale of 120 mW for mice and 250 mW for rats, an exposure time of 0.05 s, and a spot size of 50 m. Laser spots were focused with crystal covers to avoid laser beam dispersion. Bubble formation was confirmed the rupture of Bruch's membrane.

Fundus photography and fundus fluorescein angiography (FFA) was imaged using a MICRON IV fundus camera (Phoenix Laboratories USA). For FFA, animals were intraperitoneally injected with 10% sodium fluorescein at a dose of 0.01 ml per 5-6 gm body weight.

The whole procedure took about 10-15 min per animal. At end post treatment day 28 (Kimba and IVT mice; rat group) and week 25 (IV mice group)], animals were euthanized by overdose of pentobarbital for blood and tissue collection.

Electroretinography (ERG)

Animals were dark-adapted overnight (12 h), and the preparations for recordings were carried out under dim red light. Anesthesia and pupil dilation were induced as described. Animals were lightly secured to a stage with fastener strips across the upper and lower back to ensure a stable, reproducible position for ERG recordings. Body temperature was maintained between 37° C. and 38° C. with a pumped water heating pad (TP500 T/Pump; Gaymar Industries, Orchard Park, NY) fixed to the top of the stage. ERGs were recorded (Espion; Diagnosis LLC, Redwood City, Calif.) with corneal monopolar electrodes (Mayo, Aichi, Japan). A gold-cup electrode (Grass-Telefactor, West Warwick, R.I.) was placed in the mouth to serve as the reference electrode, and a silver-silver chloride electrode (Grass-Telefactor, West Warwick, R.I.) was placed in the tail to serve as the ground electrode. Recordings were performed at a wide range of stimulus intensities (3.3 to 1.0 log cd*s/m2 in 0.3-log unit increments) in dark-adapted (scotopic) condition. The response at each intensity was an average of at least five trials. Signals were band-pass filtered from 1 to 100 Hz and were acquired at 1 kHz. The duration of the ERG recording session was approximately 30 minutes for each animal.

Isolectin Staining

The flattened retinas were made permeable in ice-cold 70% vol/vol ethanol for 20 minutes and then in PBS/1% Triton X-100 for 30 minutes. Retinas were incubated with AlexaFluor 568-conjugated *Griffonia simplicifolia* isolectin B4 (5 µg/mL; Invitrogen-Molecular Probes, Eugene, Oreg.) in 1×PBS overnight at 4° C. for staining of the vasculature. Then retinas were rinsed three times in 1×PBS for 10 min each and mounted in antifade medium (Prolong Antifade Kit (P7481); Invitrogen-Molecular Probes) and was sealed with the coverslip. Images of retinal vasculature were captured with fluorescence imaging and confocal microscopy (Live Cell TIRF System and AiR confocal microscope; Singapore Bio Imaging Centre-Nikon Imaging Centre, Singapore).

Results

Our study result showed that Angio-3 peptide significantly attenuates the retinal angiogenesis in KIMBA mice (FIG. 1A-D). Eylea (positive control) is only effective for 4 weeks post treatment when commenced treatment at 6 weeks of old Kimba mice via IVT. However, Angio-3 (test peptide) is effective for up to 16 weeks post treatment (FIG. 2A-D). This data indicates the long duration of Angio-3 efficacy in mice model Laser-induced mice model study demonstrated that Angio-3 peptide significantly attenuates the retinal and choroidal angiogenesis via I/V route by single dose till week 10 (FIG. 3A-C). The systemic route did not affect the natural wound healing process, menstrual cycle and behavioural change, which shows that Angio-3 is safe to given via IV route. Angio-3 also significantly attenuates the retinal and choroidal angiogenesis than anti-VEGF via IVT route (FIGS. 4A-B). Angio-3 also shows significantly attenuates the retinal and choroidal angiog than anti-VEGF via sub-lingual route (FIGS. 5A-C). In addition, our study shows that Angio-3 could be a potential long acting anti-angiogenic for retinal and choroidal angiogenesis diseases (FIGS. 2 and 3).

This peptide can be administered as intravenous or via IVT application for prevention or treatment of retinal angiogenic diseases. Our animal model study result confirms that Angio-3 is a long-acting anti-VEGF, which has potential benefit than current drug in the market.

Example 3. Efficacy of Modified Angio-3 Peptides on Retinal Angiogenic Diseases

In B6J mice, single intravitreous (IVT) injection of 100 ng, 1 µg, 5 µg PEP-Q, PEP-N (modified Angio-3), Angio-3 and Eylea were executed and this was tested in Prevention mode (before laser) Method of LIser induced CNV model and injection was described as above.

Figure 11A:
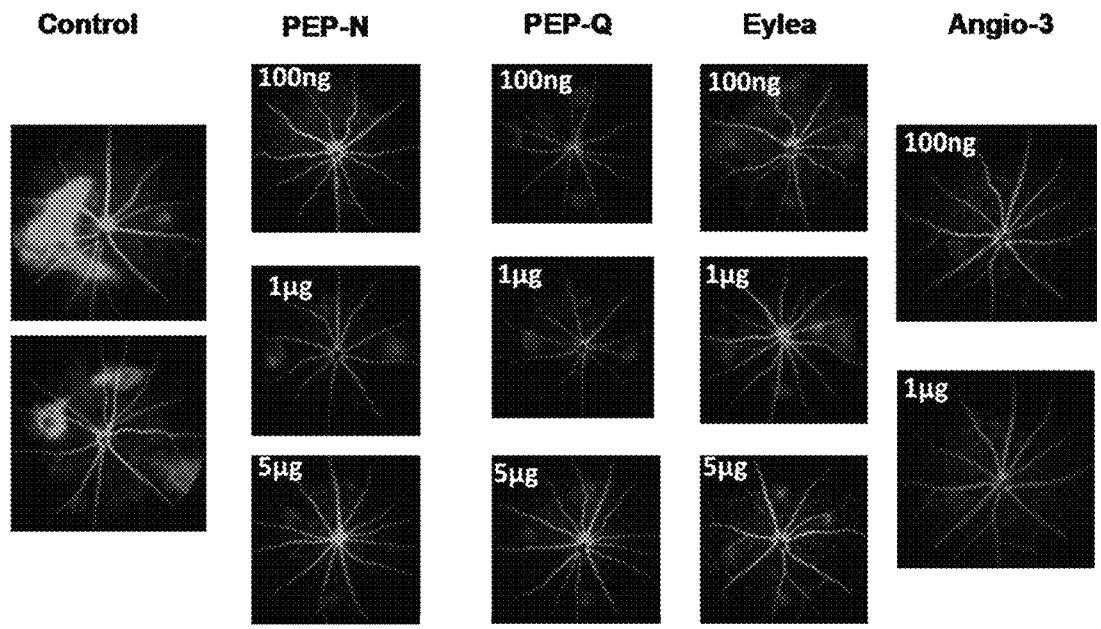
Figure 11B:
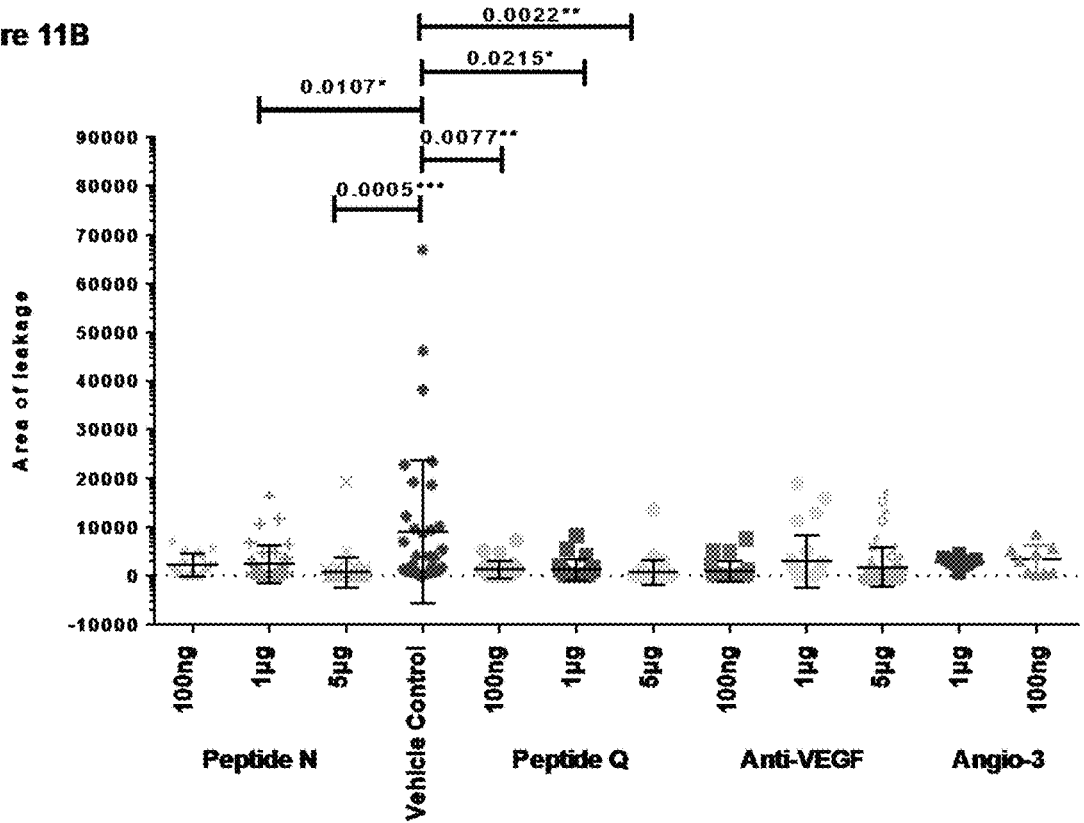

The study result showed that chemical modified angio-3 peptides: PEP-N and PEP-Q peptide significantly attenuates the choroidal angiogenesis in laser-induced CNV mice via single intravitreal injection at dose 100 ng, 1 g, and 5 µg. (FIGS. 11A-B). The original Angio-3 (100 ng and 1 µg) and positive control Eylea© at the same dose (100 ng, 1 g, and 5 µg) also shows superior efficacy that is similar to PEP-Q and PEP-N (FIG. 11; Table 2). PEP-Q and PEP-N could be a potential long acting anti-angiogenic for retinal and choroidal angiogenic diseases.

TABLE 2

Summary of PEP-N, PEP-Q, Angio-3 and Eylea on Area of Leakage

| Groups | | Area of Leakage (mean) | | % Reduction |
|---|---|---|---|---|
| | | Week 1 | Week 4 | |
| Vehicle control | | 14738.20 | 9110.67 | 0% |
| PEP-N | 100 ng | 11287.40 | 2237.13 | 42.00% |
| | 1 µg | 12808.95 | 2402.54 | 43.06% |
| | 5 µg | 8251.43 | 749.71 | 52.73% |
| PEP-Q | 100 ng | 9987.09 | 1283.52 | 48.96% |
| | 1 µg | 13444.14 | 1271.30 | 52.36% |
| | 5 µg | 12839.27 | 742.03 | 56.04% |
| Eylea | 100 ng | 10273.37 | 3433.52 | 28.40% |
| | 1 µg | 12502.09 | 3005.85 | 37.77% |
| | 5 µg | 11724.39 | 1834.08 | 46.17% |

TABLE 2-continued

Summary of PEP-N, PEP-Q, Angio-3 and Eylea on Area of Leakage

| Groups | | Area of Leakage (mean) | | % Reduction |
|---|---|---|---|---|
| | | Week 1 | Week 4 | |
| Angio-3 | 100 ng | 7404.61 | 3334.89 | 50.03% |
| | 1 μg | 6214.08 | 2867.88 | 48.92% |

This two Angio-3 peptides, PEP-Q and PEP-N, can be administered as intravitreal injection for prevention or treatment of retinal angiogenic diseases. The animal model study result confirmed that chemically-modified Angio-3 peptides, PEP-Q and PEP-N, are novel and has potentially greater benefit than current drugs on the market.

Example 4. Mechanistic Study of Angio-3

Effect of Angio-3 on VEGF Induced Proliferation of HRMEC Cells

2000 HRMEC cells were seeded in 96-well plates in 100 μl of media and placed in a $CO_2$ incubator at 37° C. To evaluate the effect the compounds have on VEGF-induced HRMEC proliferation, cells were treated with 10 ng/ml $VEGF_{165}$ or 50 ng/ml $VEGF_{165}$ in the presence of different concentrations of Angio-3 after serum starved in EBM-2 supplemented with 0.5% FBS overnight. 300 μg/ml Avastin was used as a positive control. Alamar-Blue assay was performed after 3 days of treatment.

HRMEC cells were incubated with different concentrations of compounds in the presence or absence of $VEGF_{165}$ for 3 days. Results showed that HRMEC proliferation was induced by 10 ng/ml and 50 ng/ml of $VEGF_{165}$. 300 μg/ml Avastin was sufficient to inhibit VEGF induce proliferation. However, Angio-3 showed no effect on VEGF induced proliferation at all three concentrations tested (FIGS. 12A and B).

Effect of Angio-3 on HRMEC Cells Migration

Transwell migration assays were performed in a 24-well cells culture plate containing 8.0 μm pore size inserts. HRMEC cells were serum starved overnight prior of assay. The lower chamber were filled with EBM-2, EBM-2 supplemented with 50 ng/ml $VEGF_{165}$ plus different concentrations of inhibitors. $1\times10^5$ Cells in EBM-2 were seeded in the upper chamber. Cells were allowed to migrate to the other side of membrane for overnight at 37° C. Cells on top of the membrane were wiped off and cells migrated to the other side were fixed and stained with 0.4% crystal violet. Cell numbers were counted under a 10× objective for 5 randomly selected fields.

The results showed that HRMEC cells migration was strongly induce by $VEGF_{165}$. Migration stimulated by VEGF was completely blocked by 300 μg/ml Avastin 300 μg/ml. 300 μg/ml and 600 μg/ml Angio-3 also showed a moderate inhibitory effect on VEGF induced migration (FIGS. 13A-B).

Effect of Angio-3 on HRMECs Tube Formation

Cold 50 μl matrigel GFR (BD Biosciences) was added into 96-well plates, and the plates were incubated at 37° C. for 1 h to allow gel formation. HRMEC ($1\times10^5$/well) in EBM-2, EBM-2 supplemented with 50 ng/ml $VEGF_{165}$ with or without different concentrations of Angio-3 were then plated on the matrigel, 300 μg/ml Avastin was used as a positive control. After overnight incubation, 5 randomly selected fields of the network growth area of the cells were photographed using an inverted phase contrast photomicroscope. Tube networks were quantified using Image J Angiogenesis Analyzer.

Figure 14:
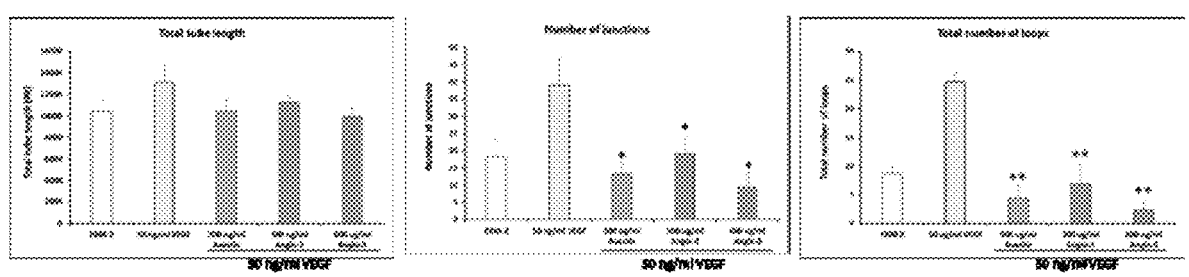
Figure 14:
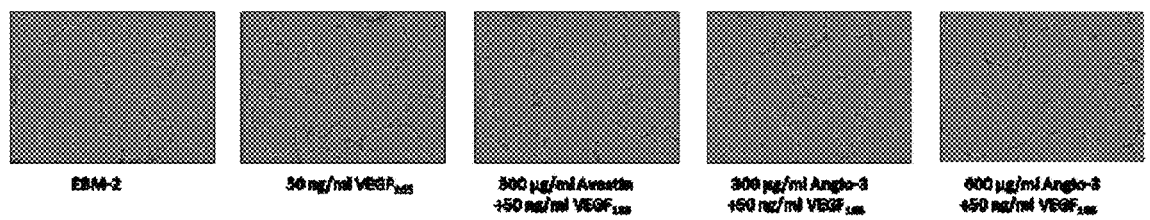

Effect of Angio-3 on VEGF induced HRMEC cells tube formation was examined and quantified in term of total tube length, number of junctions and number of loops. FIG. 14 showed that VEGF induced endothelial cells tube formation network was strongly inhibited by all drug tested.

FIGS. 15A and 15B show that Angio-3 induced human umbilical vein endothelial cells (HUVECs) apoptosis in the presence of both VEGF and bFGF. FIG. 15A showed Angio-3 induced HUVEC apoptosis in the presence of 20 ng/ml VEGF in a dose-dependent manner. FIG. 15B showed that Angio-3 induced HUVEC apoptosis in the presence of 20 ng/ml bFGF in a dose-dependent manner. * represents $p<0.05$, $n=3$.

FIGS. 16A and 16B show that Angio-3 inhibited HUVEC proliferation stimulated by VEGF and bFGF. FIG. 16A shows Angio-3 suppressed HUVEC proliferation induced by 20 ng/ml VEGF in a dose-dependent manner. FIG. 16B shows Angio-3 suppressed HUVEC proliferation induced by 20 ng/ml bFGF in a dose-dependent manner. * represents $p<0.05$, $n=3$.

Figure 17:
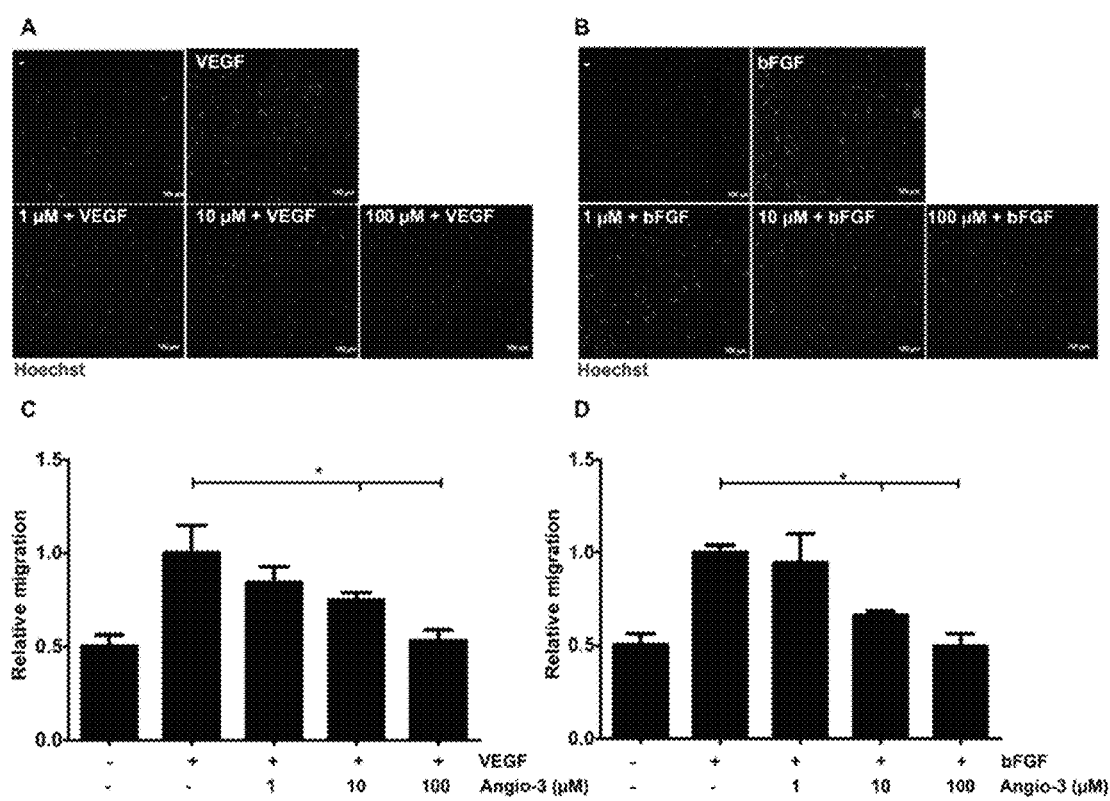

FIGS. 17 A-D show Angio-3 inhibited VEGF and bFGF-induced EC migration and inhibits capillary network formation. FIGS. 17 A and 22 C show Angio-3 suppressed HUVEC chemotactic migration induced by 20 ng/ml VEGF in a dose-dependent manner. Migrated cells were stained with Hoechst, imaged and counted. FIGS. 17 B and 22 D show Angio-3 suppressed HUVEC chemotactic migration that was induced by 20 ng/ml bFGF in a dose-dependent manner. Migrated cells were stained with Hoechst, imaged and counted.

Figure 18:
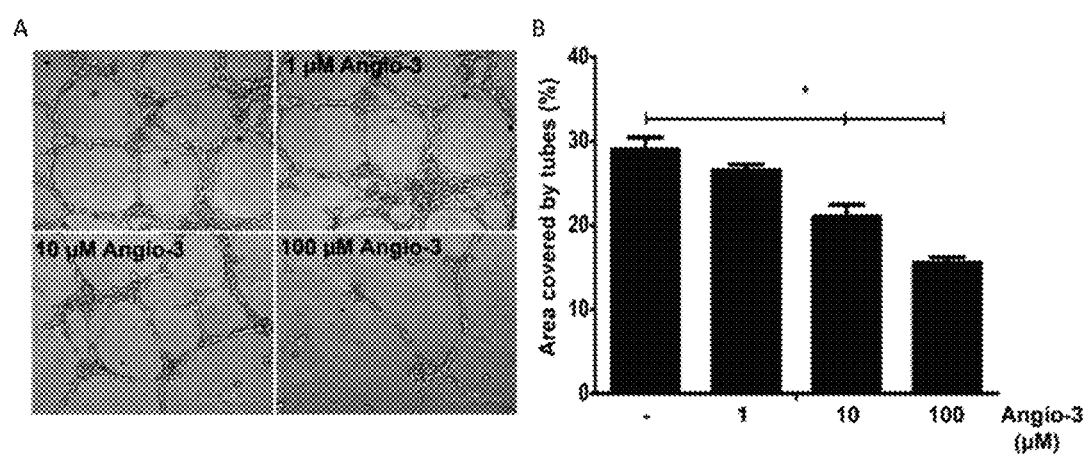

FIG. 18 shows Angio-3 inhibited HUVEC capillary network formation on Matrigel. HUVECs were pre-incubated with increasing doses of Angio-3 for 30 min prior to seeding onto Matrigel and cultured under complete EC growth media. HUVEC tube formation was imaged after 6 h of incubation. Percentage area covered by HUVEC tubes were quantified as the level of tube formation. n=3; * represents significant reduction compared to control at P<0.05 by one-way ANOVA.

FIGS. 19A, 19B and 19C show Angio-3 is a novel anti-permeability agent that can inhibit VEGF-induced vascular permeability (VP) with multiple endothelial cell types. In FIG. 19A, post-confluent HUVEC monolayers were treated with increasing concentrations of Angio-3 or medium alone. The results show that Angio-3 inhibited VEGF-induced permeability across confluent HUVECs in a dose-dependent manner without affecting the basal level permeability. In these experiments, post-confluent HUVEC monolayers were pre-treated with Angio-3 for 30 minutes prior to stimulation with 100 ng/ml VEGF. In FIG. 19B, Post-confluent HMVEC monolayers were treated with increasing concentrations of Angio-3 or medium alone. The results show that Angio-3 inhibited VEGF-induced permeability across confluent human dermal microvascular endothelial cells (HMVECs) in a dose-dependent manner without affecting the basal level permeability. In FIG. 19C, post-confluent HREC monolayers were treated with Angio-3 and VEGF for 3 h. The results show that Angio-3 inhibited VEGF-induced permeability across confluent human retinal endothelial cells (HRECs) in a dose-dependent manner without affecting the basal level permeability. * represents $p<0.05$, $n=3$.

FIGS. 20A and 20B show Angio-3 inhibited local VEGF-induced dermal vascular permeability in mice. In FIG. 20A, Angio-3 was administered via intradermal injection to mice and the results show that Angio-3 inhibited VEGF-induced dermal permeability in a dose-dependent manner within 15 min. The dermal permeability was visualized by Evans blue dye extravasation. In FIG. 20B, dye extravasation was quantified by formamide extraction of the dye and measuring OD 610. n=5 animals per group, * represent significantly increased as compared with the simultaneous control at p<0.05.

Figure 21:
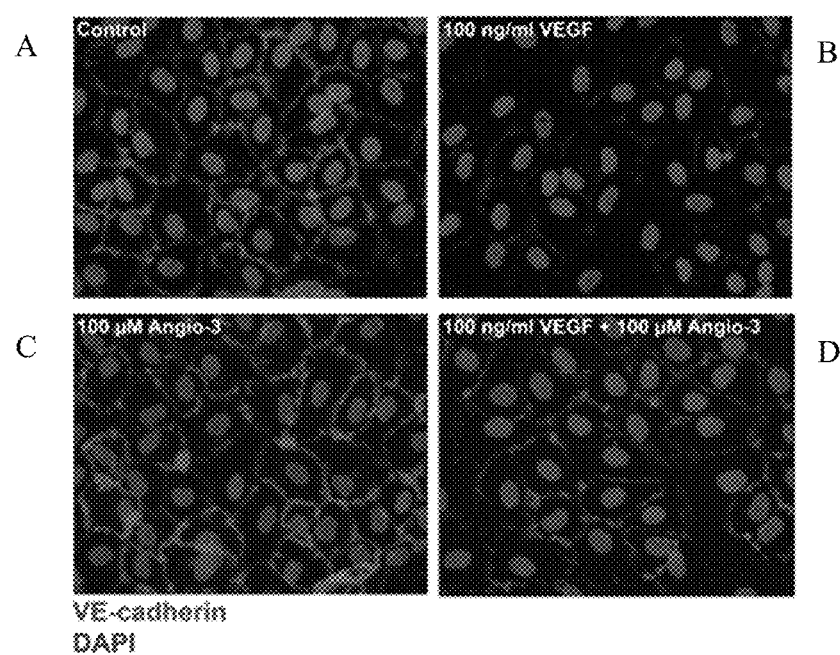

FIG. 21 shows Angio-3 prevented VEGF-induced dissociation of Vascular endothelial ("VE")-cadherin from Adherens junctions (AJs) on HUVECs. Confluent HUVECs were stimulated with 100 ng/ml VEGF to induce VE-cadherin dissociation from the AJs. The HUVECs confluent monlayes were pre-treated by 100 µM Angio-3 prior to VEGF stimulation. VE-cadherin is stained by antibody and DAPI was used to counter-stain the nucleus. Angio-3 can interferes with the ability of VEGF to induce VE-cadherin dissociation from AJs.

Figure 22:
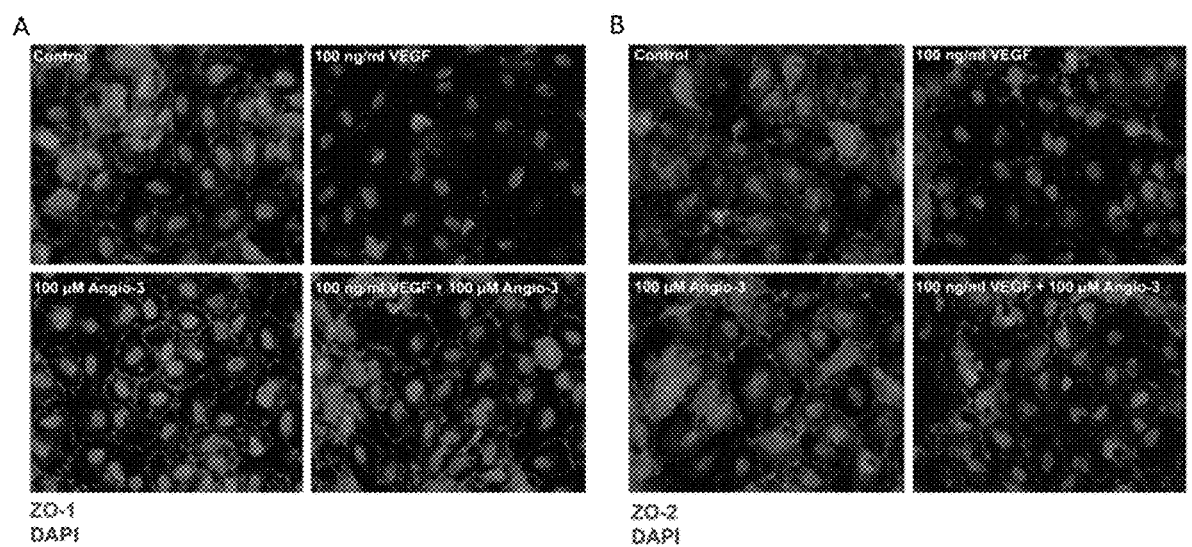

FIG. 22 shows Angio-3 suppressed VEGF-induced dissociation of tight junction (TJ) proteins ZO-1 and ZO-2 from TJs in HUVECs. HUVEC cells Cells were treated as described above and stained with an ZO-1 antibody or a ZO-2 antibody, and counter-stained with DAPI to show the nucleus. The results show that VEGF induces the TJ protein ZO-1 and ZO-2 to dissociate from the TJs of confluent HUVEC monolayers. Pre-treatment of Angio-3 (100 µM) can suppress this VEGF function.

Figure 23:
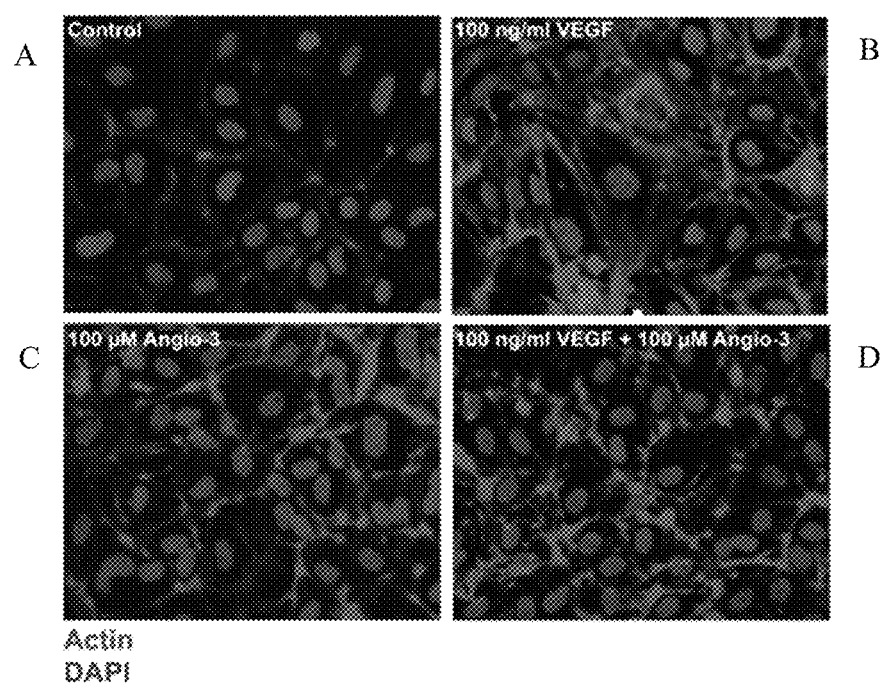

FIG. 23 shows Angio-3 suppressed VEGF-induced actin stress fiber formation in HUVECs. However, in the absence of VEGF, Angio-3 promoted cortical actin fiber formation.

Example 4. Retinal Function Tests in KIBA Mice Overexpressing hVEGF

Eight-week-old KIBA mice that overexpress hVEGF were dark-adapted overnight (for at least 12 hours) and all the procedures were carried out under dim red light. Mice were anesthetized with a combination of ketamine (20 mg/kg body weight) and xylazine (2 mg/kg body weight). Pupils were dilated with a topical administration of 1% tropicamide (Alcon Laboratories, Inc., Fort Worth, Tex., USA) and 2.5% phenylephrine (Bausch and Lomb Pharmaceuticals, Inc., Tampa, Fla., USA) ophthalmic solutions.

Animals were placed in ERG recording table with body temperature controller for ERG recordings. Electroretinograms were recorded (Espion; Diagnosys LLC, Lowell, Mass., USA) with corneal monopolar electrodes. A goldcup electrode was placed in the mouth to serve as the reference electrode, and a silver-silver chloride electrode (Grass-Telefactor, West Warwick, R.I., USA) was placed in the tail to serve as the ground electrode. Recordings were performed at a wide range of stimulus intensity (−3.0 to 1.0 log cd·s/m2) in dark-adapted (scotopic) condition. The response a teach flash intensity was an average of at least five trials. Signals were band-pass filtered from 1 to 100 Hz and were acquired at 1 kHz.

ERG was recorded from 8 weeks old to 24 weeks old of mice in untreated group (naïve group). In Angio-3 IVT treated group, ERG was recorded at 8 weeks old as baseline (BL) and then 6 and 12 weeks post treatment. 2nd IVT was given at 12 weeks after 1st treatment and then followed for 8 weeks post treatment. Student's t-test was used to compare data between two groups; P<0.05 was considered to be significant. The results are shown in FIG. 24. The untreated mice has no response of both a and b-waves after 12 weeks of age. Angio-3 increased the a and b-wave responses for 6 weeks post treatment and then again increased the response for 20 weeks with second dose. This result shows that Angio-3 is rescuing the retinal function in KIBA mice.

Example 5. Testing Angio-3 in a Laser-Induced Chorodial Neovascularization (CNV) Model Developed in Cynomolgus Monkeys as an Experimental Model of Wet AMD A laser-induced choroidal neovascularization (CNV) model was developed and validated in Cynomolgus monkeys as experimental model of wet AMD. The aim was to differentiate efficacy and dose response of test peptide from Eylea (clinical compound). 5 groups of 5 male Cynomolgus monkeys were used in this study. 3 groups were dosed IVT with 2 mg Angio-3; PeptideQ (SEQ ID NO:4) and Eylea® (dose volume 50 µL) respectively. 1 group of 5 monkeys received 4 mg of PeptideQ. 1 group was served as laser control without any drug treatment. Both eyes were injected by a single IVT injection of the drugs at Day 14 after application of laser. The development of active CNV was assessed by fluorescein angiography, at Day 14 the baseline degree of neovascularization and leakiness were measured and the final fluorescein angiography assessment was performed on Day 28. Leakage area was quantified by ImageJ software. The laser volume was quantified by Spectralis-Heidelberg software using SD-OCT images. The results are shown in FIGS. 25A-F.

In this intervention study, no change in lesion severity was observed for the laser control and the change in lesion severity and laser area was significantly different for all drug treated groups as compared with control (analysis of variance [ANOVA] followed by Tukey's multiple comparison, @=p<0.05 compared with Control). Eylea shows the superior efficacy as compared to test peptides. However, Pep-Q shows dose dependent efficacy and higher dose efficacy close to Eylea.

Example 6. Effects of Angio-3 Peptides after Alkali-Burn Injury

Mice were anesthetized with the combination of 80 mg/kg ketamine and 5 mg/kg xylazine. One drop of 1% xylocaine was applied to the corneal surface for local analgesia. Round piece of filter paper, approximately 2 mm in diameter was soaked in a solution of 1 M NaOH. A piece of NaOH soaked filter paper was picked by sterile forceps. NAOH soaked filter paper was placed on the central cornea under microscope to ensure properly placing the filter paper. Left it for 30 sec to generate an acute alkali-burn of approximately 2×2 mm² in area. Filter paper was removed and then gently flushed the eye with 10 ml of 1×PBS twice to wash away residual 1 M NaOH. Only one eye of the mouse was injured and the other serving as a control. A drop of 1× Peptide Q (1% solution as test compound) or a vehicle control consisting of PBS was topically applied to the cornea. Repeated application occurred 3×/day for 7 days. At end point, clinical assessment was done as stated below and eyes were enucleated for corneal flat mount.

Figure 26:
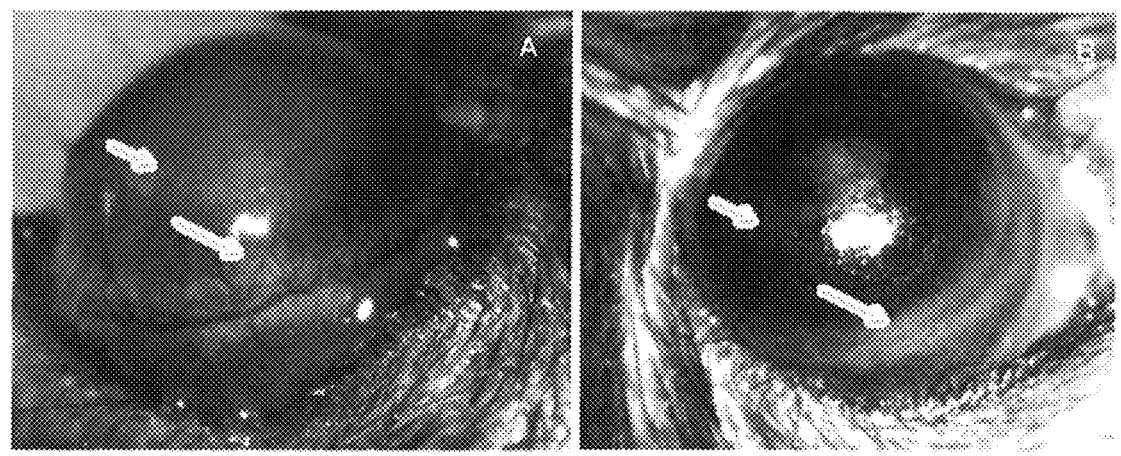

A daily examination of the mice in a blinded fashion was performed under a surgical microscope and score corneal neo-vascularization (NV) was based on corneal opacity, NV and vessel size. Two observers were scored and record a final score that was the average of the two. Score corneal opacity on a scale of 0-4. 0=completely clear; 1=slightly hazy, iris and pupil easily visible; 2=slightly opaque, iris and pupil still detectable; 3=opaque, pupils hardly detectable;

and 4=completely opaque with no view of the pupil. Score NV on a scale of 0-3. 0=no neovessels; 1=neovessels at the corneal limbus; 2=neovessels spanning the corneal limbus and approaching the corneal center; 3=neovessels spanning the corneal center. Score vessel size on a scale of 0-3. 0=no neovessels; 1=neovessels detectable under surgical microscope; 2=neovessels easily seen under surgical microscope; 3=neovessels easily seen without the microscope. Images were captured using surgical microscope camera and slit-lamp biomicroscopy. The results are shown in FIGS. 26 and 27. Peptide Q treated eyes had significantly reduced corneal NV area as compared to vehicle control eyes.

Example 7. Wound Healing in a Mouse Model

Two (2)-mm trephine was used to mark the wound size. Epithelium, basement membrane and some stromal layers were removed by peeling using forceps. Fluorescein staining to the wounded area of cornea was done from day 0 to Day 5 (n=6 mice per group from 2 independent experiments). Gentle and meticulous approach when wounding and handling mouse cornea, fluorescein was diluted, slit lamp images had to be taken within a few seconds after staining. The wound area was quantified by ImageJ software. Student's t-test was used to compare data between two groups; P<0.05 was considered to be significant. The results are shown in FIGS. 28A and 28B. Angio-3 didn't adversely affect the normal wound healing process.

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

The invention claimed is:

1. A method of treating a retinal angiogenic disease in a subject comprising:
   administering to the subject a pharmaceutically effective amount of a composition comprising a peptide consisting of the sequence Thr Pro His Thr His Gln Xaa Thr Pro Glu (SEQ ID NO:4),
   wherein the composition is administered to the subject orally, by intravenous injection, or by intravitreal injection and wherein administration treats the retinal angiogenic disease in the subject.

2. The method of claim 1, wherein the composition comprises 2 to 50 mg/kg body weight (Bwt) and is administered by intravenous injection.

3. The method of claim 1, wherein the composition comprises 0.1 μg/kg to 2 mg/kg Bwt and is administered by intravitreal injection.

4. The method of claim 1, wherein the composition comprises 2 to 10 mg/kg Bwt and is administered orally.

5. The method of claim 1, wherein the composition is administered via either intravenous (IV) or intravitreal (IVT) route at least once every 4 to 10 weeks.

6. The method of claim 1, wherein the composition is administered orally at least once daily for 1 to 2 weeks at intervals of 6 months.

7. The method of claim 1, wherein subject is not responsive to anti-vascular endothelial growth factor (VEGF) therapy.

8. The method of claim 7, wherein the anti-VEGF therapy is an anti-VEGF antibody.

9. The method of claim 1, wherein the subject has age-related macular degeneration, retinopathy, or vascular occlusion.

10. The method of claim 1, wherein the subject has diabetic retinopathy, diabetic macular edema, central retinal vein occlusion, branch retinal vein occlusion, or corneal neovascularization.

11. The method of claim 1, wherein the subject is a human.

* * * * *

SEQUENCE LISTING

```
<160> NUMBER OF SEQ ID NOS: 4

<210> SEQ ID NO 1
<211> LENGTH: 10
<212> TYPE: PRT
<213> ORGANISM: Artificial Sequence
<220> FEATURE:
<223> OTHER INFORMATION: Synthetic construct

<400> SEQUENCE: 1

Thr Pro His Thr His Asn Arg Thr Pro Glu
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic construct

<400> SEQUENCE: 2

Asn Thr Thr Glu Thr Pro His Pro His Arg
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (7)..(7)
<223> OTHER INFORMATION: Xaa can be any naturally occurring amino acid

<400> SEQUENCE: 3

Thr Pro His Thr His Asn Xaa Thr Pro Glu
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic construct
```

```
<220> FEATURE:
<221> NAME/KEY: misc_feature
<222> LOCATION: (7)..(7)
<223> OTHER INFORMATION: Xaa can be any naturally occurring amino acid

<400> SEQUENCE: 4

Thr Pro His Thr His Gln Xaa Thr Pro Glu
1               5                   10
```